United States Patent [19]

Au et al.

[11] Patent Number: 5,686,603

[45] Date of Patent: Nov. 11, 1997

[54] SULFATED POLYHYDROXY COMPOUNDS AS ANIONIC SURFACTANTS AND A PROCESS FOR THEIR MANUFACTURE

[75] Inventors: Van Au, New York, N.Y.; Robert Vermeer, Nutley; Bijan Harichian, South Orange, both of N.J.

[73] Assignee: Lever Brothers Company, Division of Conopco, Inc., New York, N.Y.

[21] Appl. No.: 434,815

[22] Filed: May 4, 1995

[51] Int. Cl.$^6$ .............................. C07H 15/02; C07H 1/00; C11D 1/12

[52] U.S. Cl. .................. 536/123.13; 536/1.11; 536/4.1; 536/17.2; 536/17.9; 536/29.1; 510/470; 510/471; 510/472

[58] Field of Search .................... 536/1.11, 4.1, 536/17.2, 17.9, 18.5, 18.7, 123, 123.13, 29.1; 510/470, 471, 472

[56] References Cited

U.S. PATENT DOCUMENTS

| | | | |
|---|---|---|---|
| 2,662,073 | 12/1953 | Mehltretter et al. | 260/102 |
| 2,670,345 | 2/1954 | Mehltretter et al. | 260/98 |
| 2,717,894 | 9/1955 | Schwartz | 260/211 |
| 2,752,334 | 6/1956 | Walton | 260/211 |
| 5,008,247 | 4/1991 | Meinetsberger | 514/23 |
| 5,296,588 | 3/1994 | Au et al. | 536/1.11 |
| 5,310,542 | 5/1994 | Au et al. | 424/52 |
| 5,312,934 | 5/1994 | Letton | 554/98 |
| 5,336,765 | 8/1994 | Au et al. | 536/18.5 |
| 5,386,018 | 1/1995 | Au et al. | 536/18.5 |
| 5,389,279 | 2/1995 | Au et al. | 424/70.19 |
| 5,401,839 | 3/1995 | Au et al. | 536/18.7 |
| 5,412,118 | 5/1995 | Vermeer et al. | 549/417 |
| 5,521,293 | 5/1996 | Vermeer et al. | 536/17.2 |

FOREIGN PATENT DOCUMENTS

| | | |
|---|---|---|
| 312086 | 4/1989 | European Pat. Off. . |
| 550106 | 7/1993 | European Pat. Off. . |
| 550278 | 7/1993 | European Pat. Off. . |
| 550281 | 7/1993 | European Pat. Off. . |
| 3941061 | 6/1991 | Germany . |
| 4318539 | 12/1994 | Germany . |
| 2-104754 | 1/1992 | Japan . |
| 2-104755 | 1/1992 | Japan . |
| 2-98857 | 1/1992 | Japan . |
| 92/06171 | 4/1992 | WIPO . |
| 94/12511 | 6/1994 | WIPO . |

OTHER PUBLICATIONS

Inoue et al., *Carbohydrate Res.*, vol. 111(1): 113–125, (1982).
Raake et al., *Thromb. Res.*, vol. 56(6): 719–730, (1989).
J. Am. Oil Chem. Soc., 202 (1952) "Surfactants and Detergents From Sulfated N–Alkyl–D–Gluconamides".
The Amer. Chem. Soc. 78:202, 2825 (1956) to Fisher et al. (1956).

*Primary Examiner*—John Kight
*Assistant Examiner*—Howard C. Lee
*Attorney, Agent, or Firm*—Ronald A. Koatz

[57] ABSTRACT

The present invention relates to sulfated polyhydroxy compounds used as anionic surfactants and to processes for their manufacture.

43 Claims, No Drawings

SULFATED POLYHYDROXY COMPOUNDS AS ANIONIC SURFACTANTS AND A PROCESS FOR THEIR MANUFACTURE

FIELD OF THE INVENTION

This invention relates to new mild anionic surfactants based on carbohydrates and a process for their manufacture. In particular, this invention relates to sulfated alkyl aldobionamides, sulfated heteroatom containing alkyl aldonamides and sulfated alkyl(glycosid) uronamides.

BACKGROUND OF THE INVENTION

The demand for mild, environmentally friendly surfactant compounds in the area of detergents, personal products, cosmetics, oral hygiene and pharmaceuticals has been steadily rising. In general, most compositions contain surfactants based on petrochemicals. Since petro-chemicals can sometimes have handling, storage, and environmental hazards associated with them, it would be most desirable to use surfactants which are instead derived from agriculturally grown materials, such as carbohydrates. These naturally occurring compounds have the distinct advantage of being readily available, inexpensive, biodegradable, aquatically favorable and optically pure.

Several new anionic surfactants based on carbohydrates have now been found, specifically sulfated alkyl aldobionamides, sulfated heteroatom containing alkyl aldonamides and sulfated alkyl(glycosid)uronamides. These compounds were found to have surfactant properties equal to, or better than, other well known anionic surfactants based on petrochemicals, thereby indicating that they are viable sound alternatives to traditional petrochemical surfactants. Thus, the ability to find a naturally derived, pure, mild sugar based anionic surfactant is a significant achievement.

BACKGROUND ART

An alkyl aldobionamide and a heteroatom containing alkyl aldonamide are generally defined as the amide of an aldonic acid (or aldonolactone) and an aldonic acid, in turn is defined as a sugar substance (e.g., any cyclic sugar) in which the pseudoaldehyde or pseudoketose group, generally found at the $C_1$ or $C_2$ position on the sugar, has been oxidized to a carboxylic acid which upon drying may cyclize to an aldonolactone. Methods of preparing such aldonic acids and aldonolactones are well known in the art and are described in EP 0,142,725 (1985) to Saito, et al.; EP 0,232, 202 (1986) and EP 0,233,816 (1987) to Fuertes et al.; JP 62/269728 (1987) to Kimura, et al.; Biotechnology Letters 6:487 (1984) to Chang, et al.; Biotechnology Letters 9:252 (1987) to Burdick, et al.; German Pat. No. 2,911,192 (1980) and U.S. Pat. No. 4,460,686 (1984) to Hartmeier and Appl. Microbiol. Biotechnol. 21:356 (1985) to Seiskari, et al. all of which are incorporated herein by reference. Aldonamides may be based on compounds comprising one saccharide unit (e.g., glyceramides, ribonamides, gluconamides or glucoheptonamides), two saccharide units (e.g., lactobionamides, maltobionamides, melibionamides, cellobionamides, gentiobionamides or D-glucosylpyranosyl-(1–5)-D-arabinonamides) or on compounds comprising more than two saccharide units (maltotrionamides or maltopentonamides). Any carbohydrate can be used to prepare an aldonamide compound, as long as the sugar has a pseudoaldehyde or pseudoketose group available for oxidation to a aldonic acid or aldonolactone.

The alkyl aldobionamides and the heteroatom containing alkyl aldonamides serve as substrates for conversion into the corresponding sulfated sugar based anionic surfactant, specifically sulfated alkyl aldobionamides and sulfated heteroatom containing alkyl aldonamides.

An alkyl(glycoside)uronamide is generally defined as the amide of an uronic acid (or uronolactone) and an uronic acid, in turn is defined as a sugar substance (e.g., any cyclic sugar) in which the terminal primary hydroxyl group, generally found at the $C_6$ position on a hexose sugar, has been oxidized to a carboxylic acid which upon drying may cyclize to an uronolactone. Uronamides may be based on compounds comprising one saccharide unit (e.g., glucopyranoside uronamides, glucofuranose uronamides, galactopyranose uronamides or galactofuranoside uronamides) or they may be based on compounds comprising two or more saccharide units (e.g., 4-O-β-galactopyranosyl-D-glucopyranoside uronamide [lactoside uronamide], 4-O-β-glucopyranosyl-D-glucopyranose uronamide [maltose uronamide] or maltotriose uronamide). Any carbohydrate can be used to prepare an uronamide compound, as long as the sugar has terminal primary hydroxyl group available for oxidation to a uronic acid or uronolactone.

The alkyl(glycosid)uronamides serve as substrates for conversion into the corresponding sulfated sugar based anionic surfactant, specifically sulfated alkyl(glycosid) uronamides.

While certain alkyl aldobionamides, heteroatom containing alkyl aldonamides and alkyl(glycosid)uronamides are known in the art, there is no teaching or suggestion of the sulfated alkyl aldobionamides, sulfated heteroatom containing alkyl aldonamides and sulfated alkyl(glycosid) uronamides of the present invention. In particular, there is no teaching or suggestion that such sulfated compounds could be mild or that such compounds are more soluble and higher foaming than their unsulfated counterparts.

U.S. Pat. No. 5,389,279, U. S. Pat. No. 5,296,588, EP Application No. 550,281, EP Application No. 550,278 and EP Application No. 550,106 to Au et al., U.S. Pat. No. 2,662,073 to Mehltretter et al. and U.S. Pat. No. 2,752,334 to Walton teach methods of preparing alkyl aldonamides/ aldobionamides and/or compositions comprising them. Again, the sulfated analogs of these compounds are not taught in any of these references, nor is there any teaching or suggestion that such sulfated compounds could be mild or more soluble and better foaming than the non-heteroatom sulfated counterparts.

U.S. Ser. No. 981,644 (also filed as WO 94/12511) to Vermeer et al. teach methods of preparing heteroatom containing alkyl aldonamides. The sulfated analogs of these compounds, however, are not taught in these references, nor is there any suggestion that such sulfated compounds could be mild or more soluble and better foaming than the non-heteroatom sulfated counterparts. In U.S. Pat. No. 2,670,345 and in the J. Am. Oil Chem. Soc., 202 (1952) to Mehltretter et al. teach non-heteroatom monosaccharide sulfated alkyl aldonamide compounds as surfactants for detergent applications. This reference fails to describe or teach sulfated heteroatom containing alkyl aldonamides and sulfated disaccharide alkyl aldobionamides of the invention. The monosulfated heteroatom containing alkyl aldonamides and monosulfated alkyl aldobionamides have been shown to be more soluble and better foaming than non-heteroatom sulfated aldonamides of U.S. Pat. No. 2,670,345 which require a higher level of sulfation for water solubility. Also, higher levels of sulfation often produces higher amounts of di-, triand polysulfated products which generally biodegrade at a slower rate. Therefore, the monosulfated heteroatom containing alkyl aldonamides and monosulfated alkyl aldobionamides of the present invention represent a class of aldonamide compound that is significantly improved over prior art sulfated alkyl aldonamides in terms of solubility, foaming and rate of biodegradation.

U.S. Pat. No. 5,008,247 to Meinetsberger teach polysulfated bis-aldonamide compounds as medicaments for pharmaceutical applications. While this paper does teach bis-alkyl aldonamide compounds containing heteroatoms, some of which are sulfated, there is no teaching or suggestion of the compounds of the present invention. The sulfated heteroatom containing alkyl aldonamides of the present invention are monomeric in nature (structurally very different), whereas the polysulfated bis-aldonamide compounds of U.S. Pat. No. 5,037,973 are dimeric in nature (too hydrophilic, unbalanced) and would not be considered as surfactants that are more soluble and better foaming than the sulfated non-heteroatom aldonamide counterparts.

The Amer. Chem. Soc., 78:202, 2825 (1956) to Fieser et al. teaches alkyl(methyl β-D-glucofuranosid)uronamides as potential emulsifying agents. Within this reference it is taught that such compounds have no emulsifying properties and little or no water solubility, hence a poor foaming profile. There is no teaching or suggestion of the sulfated alkyl(glycosid)uronamides of the present invention, in particular there is no teaching or suggestion that such a class of surfactant could be mild or more soluble and better foaming than their unsulfated counterparts.

DE 3,941,061 to Fabry teaches sulfated alkyl sorbitan esters as emulsifiers and surfactants for cosmetic, food and pharmaceutical applications. JP 2-98857, JP 2-104754 and JP 2-104755 to Fujio teach sulfated alkylpolyglycosides as surfactants for various applications. U.S. Pat. No. 2,717,894 to Schwartz, WO 92/06171 to Dyet et al. and U.S. Pat. No. 5,312,934 teach sulfated alkyl methyl glucamides as surfactants for detergent applications. These references teach sulfated sugar surfactants in general, but are otherwise unrelated to the compounds of the invention.

There is clearly no teaching or suggestion of the sulfated alkyl aldobionamides, sulfated heteroatom containing alkyl aldonamides and sulfated alkyl(glycosid)uronamides of the present invention, in particular there is no teaching or suggestion that such a class of surfactant could be mild or more soluble and better foaming than their unsulfated counterparts.

Since most compositions are based on petrochemical ingredients, it would be most desirable to use materials which are instead naturally derived, such as carbohydrates. These renewable raw materials have the distinct advantage of being readily available, inexpensive, biodegradable, aquatically favorable and optically pure.

Thus the ability to find a naturally derived, pure, mild sugar based anionic surfactant and a viable, commercially feasible method for their manufacture is a significant achievement.

Accordingly, it is an object of the present invention to provide several novel anionic sugar-based compounds as surface-active agents that are useful for detergent, personal product (cosmetic), oral hygiene, food and pharmaceutical applications.

It is another object of the present invention to provide naturally derived, cost-effective, anionic sugar based surfactants.

It is another object of the present invention to provide anionic sugar based surfactants that dissolve readily and foam well in water.

It is still another object of the present invention to provide anionic sugar based surfactants that do not become turbid or produce sedimentation upon standing in water or in aqueous detergent, personal product (cosmetic), oral hygiene and pharmaceutical compositions.

It is still another object of the present invention to provide a viable, commercially feasible process for the manufacture of anionic sugar based surfactants.

It is the final object of the present invention to prepare solid anionic sugar based surfactants in good yield, high purity and desirable color without hydroxyl group protection, oligomerization or polymerization.

These and other objects will become readily apparent from the detailed description that follows.

SUMMARY OF THE INVENTION

This invention relates to several new anionic surfactants based on carbohydrates and a process for their manufacture. In particular, the invention relates to sulfated alkyl aldobionamides, sulfated heteroatom containing alkyl aldonamides and sulfated alkyl(glycosid)uronamides.

The present invention can be considered to be an improvement over most art known anionic surfactants. The improvement comprises providing an unexpectedly mild class of anionic surfactant that is more soluble and better foaming then their unsulfated counterparts. In addition, these compounds were found to have surfactant properties equal to, or better than, other well known anionic surfactants based on petrochemicals, thereby indicating that they are viable, sound alternatives to traditional petrochemical surfactants. Thus, the invention provides several different naturally derived, pure, mild anionic sugar based surfactants.

DETAILED DESCRIPTION OF THE INVENTION

The present invention relates to a class of environmentally friendly "green" anionic surfactants. In particular, the first embodiment of the invention relates to novel sulfated alkyl aldobionamides having the general formula:

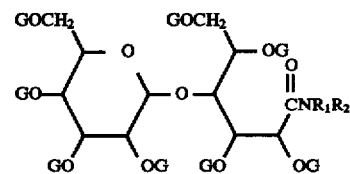

wherein:

G is a mixture of hydrogen (H) and at least one $SO_3X$ group, or a mixture of hydrogen (H), a polyoxyethylene, polyoxypropylene group and at least one $SO_3X$ group;

$R_1$ is hydrogen (H), a $C_1$–$C_{18}$ straight or branched chain, saturated or unsaturated hydrocarbon group or mixtures thereof;

$R_2$ is a $C_1$–$C_{26}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$), sulfur (S), sulfur monoxide (SO), sulfur dioxide ($SO_2$), sulfamate ($NSO_3X$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

Preferably:

G is a mixture of hydrogen (H) and at least one $SO_3X$ group, or a mixture of hydrogen (H), polyoxyethylene, polyoxypropylene and at least one $SO_3X$ group;

$R_1$ is hydrogen (H), a $C_1$–$C_8$ hydrocarbon, 2-hydroxyethyl, 2-hydroxypropyl group or mixtures thereof;

$R_2$ is a $C_6$–$C_{24}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

More preferably:

G is a mixture of hydrogen (H) and at least one $SO_3X$ group;

$R_1$ is hydrogen (H), a $C_1$–$C_6$ hydrocarbon, 2-hydroxyethyl, 2-hydroxypropyl group or mixtures thereof;

$R_2$ is a $C_8$–$C_{22}$ straight or branched chain, saturated or unsaturated hydrocarbon group that may be interrupted with at least one heteroatom selected from the group consisting of ether (O), amide ($NR_1CO$, $CONR_1$ or $NCOR_1$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

The second embodiment of the invention relates to novel sulfated heteroatom containing alkyl aldonamides of the general formula:

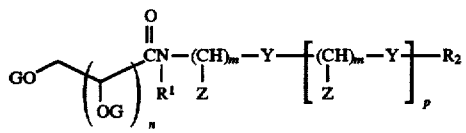

wherein:

G is a mixture of hydrogen (H) and at least one $SO_3X$ group, or a mixture of hydrogen (H), polyoxyethylene, polyoxypropylene and at least one $SO_3X$ group;

$R_1$ is hydrogen (H), a $C_1$–$C_{18}$ straight or branched chain, saturated or unsaturated hydrocarbon group or mixtures thereof;

$R_2$ is a $C_1$–$C_{26}$ straight or branched chain, saturated or unsaturated hydrocarbon group or mixtures thereof;

X is hydrogen (H), an alkali metal, alkaline earth metal, ammonium group, alkyl ammonium group, mono-, di-, or trialkanol ammonium group, basic amino acid or mixtures thereof;

Y=amine (NH), ether (O), ester (COO or OOC), amide ($NR_1CO$, $CONR_1$ or $NCOR_1$), sulfur (S), sulfur monoxide (SO), sulfur dioxide ($SO_2$), sulfamate ($NSO_3X$), hydroxy (CHOH or $C[OH]_2$) group or mixtures thereof;

n=1–8;

m=1–8;

p=0–35; and

Z=hydrogen (H) or hydrogen and at least one methyl group.

Preferably:

G is a mixture of hydrogen (H) and at least one $SO_3X$ group, or a mixture of hydrogen (H), polyoxyethylene, polyoxypropylene and at least one $SO_3X$ group;

$R_1$ is hydrogen (H), a $C_1$–$C_8$ hydrocarbon, 2-hydroxyethyl, 2-hydroxypropyl group or mixtures thereof;

$R_2$ is a $C_6$–$C_{24}$ straight or branched chain, saturated or unsaturated hydrocarbon group or mixtures thereof;

X is hydrogen (H), an alkali metal, alkaline earth metal, ammonium group, alkyl ammonium group, mono-, di-, or trialkanol ammonium group, basic amino acid or mixtures thereof;

Y=amine (NH), ether (O), ester (COO or OOC), amide ($NR_1CO$, $CONR_1$ or $NCOR_1$), hydroxy (CHOH or $C[OH]_2$) group or mixtures thereof;

n=1–6;

m=1–6;

p=0–25; and

Z=hydrogen (H) or hydrogen and at least one methyl group.

More preferably:

G is a mixture of hydrogen (H) and at least one $SO_3X$ group;

$R_1$ is hydrogen (H), a $C_1$–$C_6$ hydrocarbon, 2-hydroxyethyl, 2-hydroxypropyl group or mixtures thereof;

$R_2$ is a $C_8$–$C_{22}$ straight or branched chain, saturated or unsaturated hydrocarbon group or mixtures thereof;

X is hydrogen (H), an alkali metal, alkaline earth metal, ammonium group, alkyl ammonium group, mono-, di-, or trialkanol ammonium group, basic amino acid or mixtures thereof;

Y=ether (O), amide ($NR_1CO$, $CONR_1$ or $NCOR_1$), hydroxy (CHOH or $C[OH]_2$) group or mixtures thereof;

n=1–5;

m=1–5;

p=0–5; and

Z=hydrogen (H) or hydrogen and at least one methyl group.

The third embodiment of the invention relates to novel sulfated alkyl(glycosid)uronamides having the formulas:

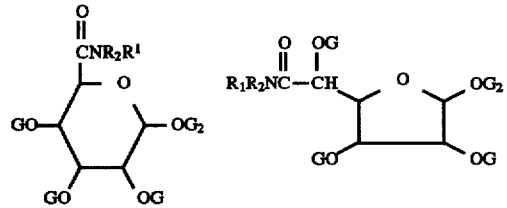

wherein:

G is a mixture of hydrogen (H) and at least one $SO_3X$ group, or a mixture of hydrogen (H), polyoxyethylene, polyoxypropylene and at least one $SO_3X$ group;

$G_2$ is a mixture of hydrogen (H) and at least one $SO_3X$ group, a mixture of hydrogen (H), polyoxyethylene, polyoxypropylene and at least one $SO_3X$ group or a mixture of a $C_1$–$C_{18}$ hydrocarbon and at least one $SO_3X$ group;

$R_1$ is hydrogen (H), a $C_1$–$C_{18}$ straight or branched chain, saturated or unsaturated hydrocarbon group or mixtures thereof;

$R_2$ is a $C_1$–$C_{26}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$), sulfamate ($NSO_3X$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

Preferably:

G is a mixture of hydrogen (H) and at least one $SO_3X$ group, or a mixture of hydrogen (H), polyoxyethylene, polyoxypropylene and at least one $SO_3X$ group;

$G_2$ is a mixture of hydrogen (H) and at least one $SO_3X$ group, a mixture of hydrogen (H), or a mixture of a $C_1$–$C_8$ hydrocarbon and at least one $SO_3X$ group;

$R_1$ is hydrogen (H), a $C_1$–$C_8$ hydrocarbon, 2-hydroxyethyl, 2-hydroxypropyl group or mixtures thereof;

$R_2$ is a $C_6$–$C_{24}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

More preferably:

G is a mixture of hydrogen (H) and at least one $SO_3X$ group;

$G_2$ is a mixture of hydrogen (H) and at least one $SO_3X$ group, a mixture of hydrogen (H), or a mixture of a $C_1$–$C_6$ hydrocarbon and at least one $SOD_3X$ group;

$R_1$ is hydrogen (H), a $C_1$–$C_6$ hydrocarbon, 2-hydroxyethyl, 2-hydroxypropyl group or mixtures thereof;

$R_2$ is a $C_8$–$C_{22}$ straight or branched chain, saturated or unsaturated hydrocarbon group that may be interrupted with at least one heteroatom selected from the group consisting of ether (O), amide ($NR_1CO$, $CONR_1$ or $NCOR_1$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

A specific example of a sulfated alkyl aldobionamide of the invention is sodium coconut D-lactobionamide monosulfate having the formula:

wherein:

G is a mixture of hydrogen (H) and one $SO_3X$ group;

$R_1$ is hydrogen (H);

$R_2$ is $C_8H_{17}$ (5%), $C_{10}H_{21}$ (7%), $C_{12}H_{25}$ (50%), $C_{14}H_{29}$ (18%), $C_{16}H_{33}$ (10%), $C_{18}H_{37}$ (6%), $C_{18}H_{35}$ (4%); and X is sodium (Na).

Another specific example of a sulfated alkyl aldobionamide of the invention is potassium dodecyl to pentadecyloxypropyl D-lactobionamide monosulfate having the formula:

wherein:

G is a mixture of hydrogen (H) and one $SO_3X$ group;

$R_1$ is hydrogen (H);

$R_2$ is $(CH_2)_3OC_{12}H_{25}$ (25%), $(CH_2)_3OC_{13}H_{27}$ (39%), $(CH_2)_3OC_{14}H_{29}$ (21%), $(CH_2)_3OC_{15}H_{31}$ (15%); and X is potassium (K).

Yet another specific example of a sulfated alkyl aldobionamide of the invention is triethanolammonium lactobionyl dodecyl glycinate monosulfate having the formula:

wherein:

G is a mixture of hydrogen (H) and one $SO_3X$ group;

$R_1$ is hydrogen (H);

$R_2$ is $CH_2COOC_{12}H_{25}$;

and X is triethanolamine ($[HOCH_2CH_2]_3NH$).

A specific example of a sulfated heteroatom containing alkyl aldonamide of the invention is sodium octyl/decyloxypropyl gluconamide monosulfate having the formula:

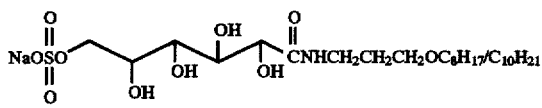

wherein:

G is a mixture of hydrogen (H) and one SO$_3$X group;

R$_1$ is hydrogen (H);

R$_2$ is C$_6$H$_{13}$ (1%), C$_8$H$_{17}$ (59%), C$_{10}$H$_{21}$ (39%), C$_{12}$H$_{25}$ (1%);

X is sodium (Na);

Y is oxygen (O);

n=4;

m=3;

p=0;

and Z=hydrogen (H).

Another specific example of a sulfated heteroatom containing alkyl aldonamide of the invention is sodium dodecyloxypropyltri(oxyethylene)glucoheptonamide monosulfate having the formula:

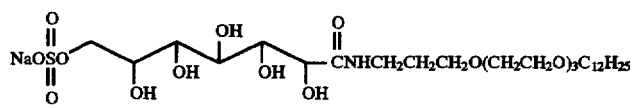

wherein:

G is a mixture of hydrogen (H) and one SO$_3$X group;

R$_1$ is hydrogen (H);

R$_2$ is C$_{12}$H$_{25}$;

X is sodium (Na);

n=5;

m=3;

p=0;

and Z=hydrogen (DH).

Yet another specific example of a sulfated heteroatom containing alkyl aldonamide of the invention is ammonium gluconyl dodecyl glycinate monosulfate having the formula:

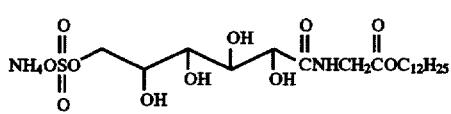

wherein:

G is a mixture of hydrogen (H) and one SO$_3$X group;

R$_1$ is hydrogen (H);

R$_2$ is CH$_2$OC$_{12}$H$_{25}$;

X is ammonium (NH$_4$);

n=4;

m=1;

p=0;

and Z=hydrogen (H).

A specific example of a disulfated alkyl aldobionamide of the invention is disodium coconut D-lactobionamide disulfate having the formula:

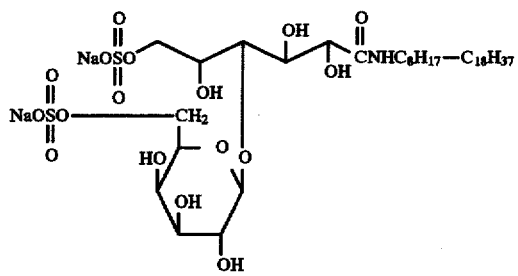

wherein:

G is a mixture of hydrogen (H) and two SO$_3$X groups;

R$_1$ is hydrogen (H);

R$_2$ is C$_8$H$_{17}$ (5%), C$_{10}$H$_{21}$ (7%), C$_{12}$H$_{25}$ (50%), C$_{14}$H$_{29}$ (18%), C$_{16}$H$_{33}$ (10%), C$_{18}$H$_{37}$ (6%), C$_{18}$H$_{35}$ (4%);

and X is sodium (Na).

A specific example of a disulfated heteroatom containing alkyl aldonamide of the invention is disodium dodecyloxypropyl gluconamide disulfate having the formula:

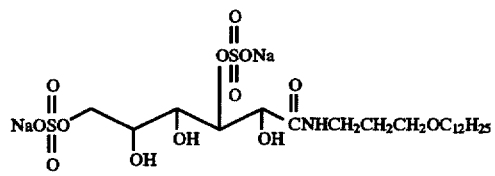

wherein:

G is a mixture of hydrogen (H) and two SO$_3$X groups;

R$_1$ is hydrogen (H);

R$_2$ is (CH$_2$)$_3$OC$_{12}$H$_{25}$;

X is sodium (Na);

n=4;

m=3;

p=0;

and Z=hydrogen (H).

A specific example of a sulfated alkyl(glycosid) uronamide of the invention is sodium coconut(methyl galactopyranosid)uronamide monosulfate having the formula:

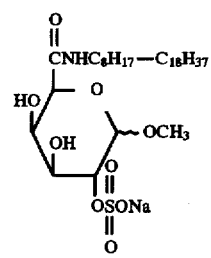

wherein:

G is a mixture of hydrogen (H) and one SO$_3$X group;

$G_2$ is methyl ($CH_3$);

$R_1$ is hydrogen (H);

$R_2$ is $C_8H_{17}$ (5%), $C_{10}H_{21}$ (7%), $C_{12}H_{25}$ (50%), $C_{14}H_{29}$ (18%), $C_{16}H_{33}$ (10%), $C_{18}H_{37}$ (6%), $C_{18}H_{35}$ (4%);

and X is sodium (Na).

Another specific example of a sulfated alkyl(glycosid) uronamide of the invention is sodium dodecyloxypropyl (methyl glucofuranosid)uronamide monosulfate having the formula:

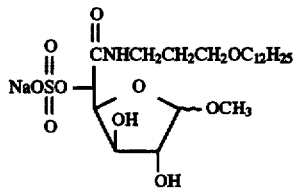

wherein:

G is a mixture of hydrogen (H) and one $SO_3X$ group;

$R_1$ is hydrogen (H);

$R_2$ is $(CH_2)_3OC_{12}H_{25}$;

$G_2$ is methyl ($CH_3$);

and X is sodium (Na).

Yet another specific example of a sulfated alkyl(glycosid) uronamide of the invention is sodium ethyl(dodecyl glucofuranosid)uronamide monosulfate having the formula:

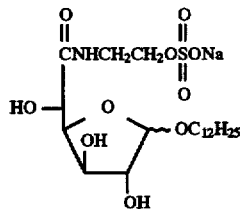

wherein:

G is a hydrogen (H);

$R_1$ is hydrogen (H);

$R_2$ is $CH_2CH_2OSO_3Na$;

$G_2$ is dodecyl ($C_{12}H_{25}$);

and X is sodium (Na).

Still another specific example of a sulfated alkyl(glycosid) uronamide of the invention is coconut aminopropyl(methyl galactopyranosid)uronamide monosulfate (from chlorosulfonic acid, sulfur trioxide, sulfuric acid and the like) having the formula:

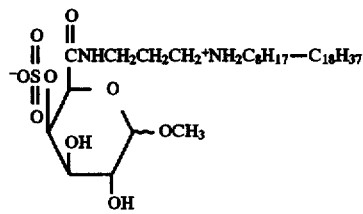 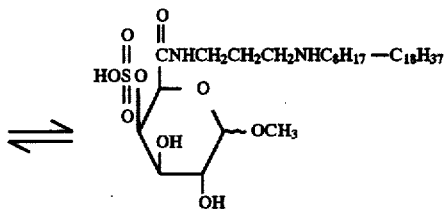

wherein:

G is a mixture of hydrogen (H) and one $SO_3X$ group;

$G_2$ is methyl ($CH_3$);

$R_1$ is hydrogen (H);

$R_2$ is $(CH_2)_3NHC_8H_{17}$ (5%), $(CH_2)_3NHC_{10}H_{21}$ (7%), $(CH_2)_3NHC_{12}H_{25}$ (50%), $(CH_2)_3NHC_{14}H_{29}$ (18%), $(CH_2)_3NHC_{16}H_{33}$ (10%), $(CH_2)_3NHC_{18}H_{37}$ (6%), $(CH_2)_3NHC_{18}H_{35}$ (4%);

and X is hydrogen (H).

Still another specific example of a sulfated alkyl(glycosid) uronamide of the invention is potassium coconutsulfamatepropyl(ethyl galactopyranosid) uronamide (from pyridine sulfur tri-oxide complex) having the formula:

wherein:

G is a mixture of hydrogen (H);

$G_2$ is ethyl ($CH_2CH_3$);

$R_1$ is hydrogen (H);

$R_2$ is $(CH_2)_3N(SO_3K)C_8H_{17}$ (5%), $(CH_2)_3N(SO_3K)C_{10}H_{21}$ (7%), $(CH_2)_3N(SO_3K)C_{12}H_{25}$ (50%), $(CH_2)_3N(SO_3K)C_{14}H_{29}$ (18%), $(CH_2)_3N(SO_3K)C_{16}H_{33}$ (10%), $(CH_2)_3N(SO_3K)C_{18}H_{37}$ (6%), $(CH_2)_3N(SO_3K)C_{18}H_{35}$ (4%);

and X is potassium (K).

A specific example of a disulfated alkyl(glycosid) uronamide of the invention is disodium coconutsulfamatepropyl(methyl galactopyranosid) uronamide monosulfate (from an excess of pyridine sulfur trioxide complex) having the formula:

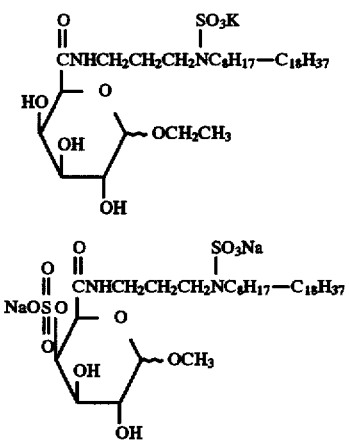

wherein:

G is a mixture of hydrogen (H) and and two $SO_3X$ groups;

$G_2$ is methyl ($CH_3$);

$R_1$ is hydrogen (H);

$R_2$ is $(CH_2)_3N(SO_3Na)C_8H_{17}$ (5%), $(CH_2)_3N(SO_3Na)C_{10}H_{21}$ (7%), $(CH_2)_3N(SO_3Na)C_{12}H_{25}$ (50%), $(CH_2)_3N(SO_3Na)C_{14}H_{29}$ (18%), $(CH_2)_3N(SO_3Na)C_{16}H_{33}$ (10%), $(CH_2)_3N(SO_3Na)C_{18}H_{37}$ (6%), $(CH_2)_3N(SO_3Na)C_{18}H_{35}$ (4%);

and X is sodium (Na).

Other examples of compounds of the invention are set forth below:

alkyloxymethyl D-gluconamide monosulfate
alkyloxyethyl D-gluconamide disulfate
alkyloxybutyl D-gluconamide trisulfate
alkyloxypentyl D-gluconamide monosulfate
alkyloxyethyloxymethyl D-gluconamide tetrasulfate
alkyldi(oxyethyl)oxymethyl D-gluconamide monsulfate
alkyldi(oxyethyl) D-gluconamide monosulfate
alkyltri(oxyethyl) D-gluconamide disulfate
alkyltetra(oxyethyl) D-gluconamide hemisulfate
alkylpenta(oxyethyl) D-gluconamide disulfate
alkylhexa(oxyethyl) D-gluconamide polysulfate
alkylhepta(oxyethyl) D-gluconamide monosulfate
alkylocta(oxyethyl) D-gluconamide monsulfate
alkyldi(oxypropyl)oxyethyl D-gluconamide monosulfate
alkyltri(oxypropyl)oxyethyl D-gluconamide monosulfate
alkylocta(oxypropyl)oxyethyl D-gluconamide trisulfate
alkyldi(oxyethyl)oxypropyl D-gluconamide disulfate
alkyltri(oxyethyl)oxypropyl D-gluconamide monosulfate
alkyltetra(oxyethyl)oxypropyl D-gluconamide monosulfate
alkylpenta(oxyethyl)oxypropyl D-gluconamide disulfate
alkylhexa(oxyethyl)oxypropyl D-gluconamide sesquisulfate
alkylhepta(oxyethyl)oxypropyl D-gluconamide disulfate
alkylocta(oxyethyl)oxypropyl D-gluconamide monosulfate
alkyloxymethyl D-lactobionamide monosulfate
alkyloxyethyl D-lactobionamide disulfate
alkyloxybutyl D-lactobionamide trisulfate
alkyloxypentyl D-lactobionamide tetrasulfate
alkyl(oxyethyl)oxymethyl D-lactobionamide pentasulfate
alkyldi(oxyethyl)oxymethyl D-lactobionamide sesquisulfate
alkyldi(oxyethyl) D-lactobionamide polysulfate
alkyltri(oxyethyl) D-lactobionamide monosulfate
alkyltetra(oxyethyl) D-lactobionamide disulfate
alkylpenta(oxyethyl) D-lactobionamide monosulfate
alkylhexa(oxyethyl) D-lactobionamide trisulfate
alkylhepta(oxyethyl) D-lactobionamide monosulfate
alkylocta(oxyethyl) D-lactobionamide monosulfate
alkyldi(oxypropyl)oxyethyl D-lactobionamide monosulfate
alkyltri(oxypropyl)oxyethyl D-lactobionamide monosulfate
alkylocta(oxypropyl)oxyethyl D-lactobionamide disulfate
alkyldi(oxyethyl)oxypropyl D-lactobionamide disulfate
alkyltri(oxyethyl)oxypropyl D-lactobionamide monosulfate
alkyltetra(oxyethyl)oxypropyl D-lactobionamide monosulfate
alkylpenta(oxyethyl)oxypropyl D-lactobionamide monosulfate
alkylhexa(oxyethyl)oxypropyl D-lactobionamide monosulfate
alkylhepta(oxyethyl)oxypropyl D-lactobionamide disulfate
alkylocta(oxyethyl)oxypropyl D-lactobionamide monosulfate
alkyloxyethyl D-maltobionamide monosulfate
alkyloxyethyloxymethyl D-maltobionamide monosulfate
alkylhexa(oxyethyl) D-maltobionamide monosulfate
alkyloxyethyl D-glucoheptonamide monosulfate
alkyloxyethyl D-melibionamide monosulfate
alkyloxyethyl D-cellobionamide monosulfate
alkyloxyethyl D-gentiobionamide monosulfate
alkyloxyethyl D-glucopyranosyl-(1–5)-D-arabinonamide monosulfate
N-gluconyl alkyl(oxyethyl)glycinate monosulfate
N-gluconyl alkyltri(oxyethyl)glycinate monosulfate
N-gluconyl alkyltetra(oxyethyl)glycinate disulfate
N-gluconyl alkyltri(oxyethyl) N-methylglycinate monosulfate
N-gluconyl dialkyldi(oxyethyl)aspartate monosulfate
N-gluconyl alkyldi(oxyethyl)alaninate monosulfate
N-gluconyl alkyltetra(oxyethyl) β-alaninate monosulfate
N-gluconyl alkyldi(oxypropyl) N-methylalaninate monosulfate
N-gluconyl alkyltri(oxyethyl) α-aminobutyrate monosulfate
N-gluconyl alkyl(oxyethyl)sarcosinate monosulfate
N-gluconyl alkyldi(oxyethyl)sarcosinate monosulfate
N-gluconyl alkyltri(oxyethyl)sarcosinate monosulfate
N-gluconyl alkyltri(oxyethyl)leucinate monosulfate
N-lactobionyl alkyldi(oxyethyl)glycinate monosulfate
N-lactobionyl alkyltri(oxyethyl)alaninate hemisulfate
N-lactobionyl alkyltetra(oxyethyl) β-alaninate monosulfate
N-lactobionyl alkyldi(oxyethyl) N-methylalaninate monosulfate
N-lactobionyl alkyltri(oxyethyl) α-aminobutyrate monosulfate
N-lactobionyl alkyltri(oxyethyl) α-aminoisobutyrate monosulfate
N-lactobionyl alkyltri(oxyethyl) ε-aminocarproate monosulfate
N-lactobionyl alkyldi(oxyethyl)sarcosinate monosulfate
N-lactobionyl alkyltri(oxyethyl)leucinate monosulfate
N-glucoheptonyl alkyl(oxyethyl)glycinate trioxyethylene ether monosulfate
N-maltobionyl alkyl(oxyethyl)glycinate tetraoxyethylene ether monosulfate
N-cellobionyl alkyl(oxyethyl)glycinate monosulfate
alkyloxypropyl D-gluconamide monooxyethylene ether monosulfate
alkyloxypropyl D-gluconamide dioxyethylene ether monosulfate
alkyloxypropyl D-gluconamide trioxyethylene ether monosulfate
alkyloxypropyl D-gluconamide tetraoxyethylene ether monosulfate
alkyloxypropyl D-gluconamide pentaoxyethylene ether hemisulfate
alkyloxypropyl D-gluconamide hexaoxyethylene ether monosulfate
alkyloxypropyl D-gluconamide heptaoxyethylene ether monosulfate
alkyloxypropyl D-gluconamide octaoxyethylene ether monosulfate
alkyloxypropyl D-gluconamide nonaoxyethylene ether monosulfate
alkyloxypropyl D-gluconamide decaoxyethylene ether disulfate
alkyloxypropyl D-gluconamide trioxypropylene ether trisulfate
alkyloxyethyl D-gluconamide dioxyethylenetrioxypropylene ether monosulfate
alkyloxyethyl D-gluconamide trioxypropylenedioxyethylene ether monosulfate
alkyloxypropyl D-lactobionamide monooxyethylene ether monosulfate
alkyloxypropyl D-lactobionamide dioxyethylene ether monosulfate
alkyloxypropyl D-lactobionamide trioxyethylene ether monosulfate
alkyloxypropyl D-lactobionamide tetraoxyethylene ether monosulfate
alkyloxypropyl D-maltobionamide dioxyethylene ether monosulfate
alkyloxypropyl D-maltobionamide pentaoxypropylene ether monosulfate
alkyloxypropyl D-maltobionamide decaoxypropylene ether monosulfate alkylamidopropyl D-lactobionamide hexaoxyethylene ether monosulfate Wherein the alkyl group contains from about 1 to about 26 carbon atoms, preferably from about 6 to about 24 carbon atoms and even more preferably from about 8 to about 22 carbon atoms and the above sulfate groups contain a counterion selected from the group consisting of hydrogen (H), alkali metal, alkaline earth metal, ammonium, alkyl ammonium, mono-, di- or tri-alkanolammonium, basic amino acid or mixtures thereof.

The $R_1$ group is most preferably hydrogen or a $C_1$ to $C_6$ alkyl group that optionally may contain a hydroxyl group, however it may also be a hydroxy $C_1$ to $C_{18}$ alkyl group or a $C_1$ to $C_{18}$ straight or branched chain, saturated or unsaturated hydrocarbon radical. The $R_1$ group may also be interrupted by a heteroatom and may have the same structure as the group attached to the nitrogen atom.

If the $R_1$ or $R_2$ group is an aliphatic radical, suitable examples include, but are not limited to methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl, linolenyl, lanolin, ricinoleyl, behenyl, abietyl, naphthenyl, erucyl, hentricontanyl, 2-ethylbutyl, 2-ethylhexyl and the like.

If the $R_1$ or $R_2$ group is interrupted by an aromatic radical, the aromatic group may be for example, benzyl or aniline. Cycloaliphatic radicals are exemplified but are not limited to cyclopentyl and cyclohexyl. Suitable mixed aromatic aliphatic radicals are exemplified by benzylpropyl, phenylethyl, phenoxyethyl and vinylbenzyl.

The G group may be a mixture of hydrogen and at least one sulfate group ($SO_3X$), or a mixture of hydrogen (H), polyoxyethylene, polyoxypropylene group and at least one sulfate group ($SO_3X$), wherein X is a hydrogen (H), an alkali metal, alkaline earth metal, ammonium group, alkyl ammonium group, mono-, di- or trialkanolammonium group, basic amino acid group or mixtures thereof.

Examples of suitable saccharides that can be converted into sulfated aldonamides, aldobionamides, and alkyl (glycosid)uronamides of the invention include, but are not limited to, aldotrioses, aldotetroses, aldopentoses, aldohexoses, 6-deoxyaldohexoses, aldoheptoses, ketotrioses, ketopentoses, ketohexoses, ketoheptoses, ketooctoses and ketononoses. Specific examples of saccharides that fall within the above class include, but are not limited to glyceraldehyde, erythrose, threose, ribose, arabinose, xylose, lyxose, allose, altrose, idose, talose, glucose, galactose, mannose, gulose, 6-deoxyallose, 6-deoxyaltrose, 6-deoxyglucose, 6-deoxygulose, 6-deoxytalose, fucose, rahmnose, glycergalactoheptose, glycerglucohepotse, glycermannoheptose, 1,3-dihydroxy-2-propanone, erythrulose, ribulose, xylulose, psicose, fructose, sorbose, tagatose, alloheptose, altro-3-heptulose, mannoheptulose, sedoheptulose, taloheptulose, glycerogalactooctulose, glycermannooctulose, erythrogalactononulose, erythroglucononulose, sucrose, isomaltose, isomalt, isomaltulose(palatinose), trehalulose, 3-ketosucrose, leucrose, lactulose, gentiobiose, maltose, isomaltose, isomalt, isomaltulose(palatinose), α,α-trehalose, laminarabiose, xylobiose, inulobiose, mannobiose, chondrosine, 3-ketosucrose, turnanose, trehalose, raffinose, planteose, melezitose, gentianose, lactose, melibose, cellobiose, triglucose(maltotriose), cellotriose, panose, starchyose, verbascose, cyclohexaamylose, maltoheptanose, cellodextrin, amylose, amylodextrin, dextran, high dextrose corn syrup, high fructose corn syrup, high maltose corn syrup, xylans, mannans, starch, hemicellulose, cellulose and mixtures thereof. The saccharide may be acyclic or cyclic (including furanose, pyranose, septanose rings or mixtures thereof), have the D or L configuration and contain a α or β group or mixtures thereof at the anomeric position.

When an amino group is present it may be converted to the corresponding salt by reaction with, for example an organic or inorganic acid such as hydrochloric acid, sulfuric acid, phosphoric acid, boric acid, oxalic acid, malonic acid, glutaric acid, adipic acid, sebacic acid, tricarballylic acid, butanetetracarboxylic acid, itaconic acid, maleic acid, malic acid, fumaric acid, citraconic acid, glutaconic acid, bis (hydroxymethyl)propionic acid, tartaric acid, citric acid, formic acid, lactic acid, acetic acid, benzoic acid, methanesulfonic acid, ethanesulfonic acid, toluenesulfonic acid and mixtures thereof or by reaction with, for example an alkylating agent such as chloromethane, dimethyl sulfate, diethyl sulfate and benzyl chloride. It should be noted that sulfated amino containing polyhydroxy compounds of the invention [e.g. coconut aminopropyl(methyl galactopyranosid) uronamide monosulfate] are generally amphoteric in nature and can be neutral at pH 7 and anionic at pH's above 7.

The fourth embodiment of the invention relates to a new and improved process for the manufacture of sulfated alkyl aldobionamides, sulfated heteroatom containing alkyl aldonamides and sulfated alkyl(glycosid)uronamides.

Method of Manufacture

In the forth embodiment of the invention, a process for the manufacture of the sulfated alkyl aldobionamides, sulfated heteroatom containing alkyl aldonamides and sulfated alkyl (glycosid)uronamides is described. In general, compounds of the invention are obtained by sulfating nonionic sugar amides such as alkyl aldobionamides, heteroatom containing alkyl aldonamides and alkyl(glycosid)uronamides by means of sulfating agents composed of at least one compound selected from a group comprising of chlorosulfonic acid, sulfuric acid, oleum, sulfamic acid, sulfur trioxide and sulfur trioxide Lewis base complexes. In general, chlorosulfonic acid or sulfur trioxide are preferred for industrial production.

It has been found, in accordance with the process of this invention, that novel anionic sugar based surfactants may be readily prepared by reacting alkyl aldobionamides, heteroatom containing alkyl aldonamides or alkyl(glycosid) uronamides with a suitable sulfating agent in the presence of a solvent at room temperature (step A), followed by neutralization with base (step B). The invention can be more readily understood when reference is made to the general equations (I) & (II);

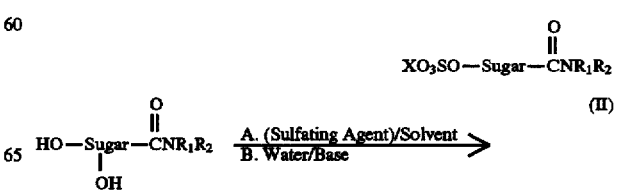

-continued

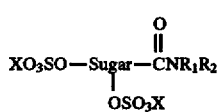

Examples of alkyl aldobionamides suitable for this method include, but are not limited to methyl lactobionamide, ethyl lactobionamide, propyl lactobionamide, butyl lactobionamide, pentyl lactobionamide, hexyl lactobionamide, heptyl lactobionamide, octyl lactobionamide, nonyl lactobionamide, decyl lactobionamide, dodecyl lactobionamide, tridecyl lactobionamide, tetradecyl lactobionamide, pentadecyl lactobionamide, hexadecyl lactobionamide, octadecyl lactobionamide, coco lactobionamide, soya lactobionamide, tallow lactobionamide, tall oil lactobionamide, castor lactobionamide, corn lactobionamide, cottonseed lactobionamide, palm lactobionamide, rapeseed lactobionamide, octenyl lactobionamide, nonenyl lactobionamide, decenyl lactobionamide, undecenyl lactobionamide, dodecenyl lactobionamide, tridecenyl lactobionamide, tetradecenyl lactobionamide, pentadecenyl lactobionamide, hexadecenyl lactobionamide, octadecenyl (oleyl)lactobionamide, linoleyl lactobionamide, linolenyl lactobionamide, $C_1-C_{26}$ alkyloxypropyl lactobionamide, $C_1-C_{26}$alkyloxypropylamidopropylmethyl lactobionamide, $C_1-C_{26}$ alkyloxypropyloxyethyl lactobionamide, $C_1-C_{26}$alkyloxypropyldi(oxyethyl)lactobionamide, $C_1-C_{26}$ alkyloxypropyltri(oxypropyl)lactobionamide, $C_1-C_{26}$ alkylpoly(oxyethyl)lactobionamide, $C_1-C_{26}$ alkylpropylpoly(oxyethyl)lactobionamide, $C_1-C_{26}$alkylpropylpoly(oxypropyl)lactobionamide, $C_1-C_{26}$alkylpoly(oxyethyl)poly(oxypropyl)lactobionamide, $C_1-C_{26}$alkylamidopropylmethyllactobionamide, ethoxylated $C_1-C_{26}$ alkyl lactobionamide, propoxylated $C_1-C_{26}$ alkyl lactobionamide, ethoxylated/propoxylated $C_1-C_{26}$ alkyl lactobionamide, propoxylated/ethoxylated $C_1-C_{26}$ alkyl lactobionamide, methyl maltobionamide, ethyl maltobionamide, propyl maltobionamide, butyl maltobionamide, pentyl maltobionamide, hexyl maltobionamide, heptyl maltobionamide, octyl maltobionamide, nonyl maltobionamide, decyl maltobionamide, dodecyl maltobionamide, tridecyl maltobionamide, tetradecyl maltobionamide, pentadecyl maltobionamide, hexadecyl maltobionamide, octadecyl maltobionamide, coco maltobionamide, soya maltobionamide, tallow maltobionamide, tall oil maltobionamide, castor maltobionamide, corn maltobionamide, cottonseed maltobionamide, palm maltobionamide, rapeseed maltobionamide, octenyl maltobionamide, nonenyl maltobionamide, decenyl maltobionamide, undecenyl maltobionamide, dodecenyl maltobionamide, tridecenyl maltobionamide, tetradecenyl maltobionamide, pentadecenyl maltobionamide, headecenyl maltobionamide, octadecenyl(oleyl)maltobionamide, linoleyl maltobionamide, linolenyl maltobionamide, $C_1-C_{26}$ alkyloxypropyl maltobionamide, $C_1-C_{26}$ alkyloxypropylamidopropylmethyl maltobionamide, $C_1-C_{26}$ alkyloxypropyloxyethyl maltobionamide, $C_1-C_{26}$ alkyloxypropyldi(oxyethyl)maltobionamide, $C_1-C_{26}$ alkyloxypropyltri(oxypropyl) $C_1-C_{26}$alkylpoly(oxyethyl)maltobionamide, $C_1-C_{26}$alkyloxypropylpoly(oxyethyl)maltobionamide, $C_1-C_{26}$poly(oxyethyl)poly(oxypropyl)maltobionamide, $C_1-C_{26}$alkylamidopropylmethyl maltobionamide, ethoxylated $C_1-C_{26}$alkyl maltobionamide, propoxylated $C_1-C_{26}$alkyl maltobionamide, ethoxylated/propoxylated $C_1-C_{26}$ alkyl maltobionamide, propoxylated/ethoxylated $C_1-C_{26}$ alkyl maltobionamide, $C_1-C_{26}$alkylsulfodioxidepropyl lactobionamide, $C_1-C_{26}$ alkylsulfomonoxidepropyl lactobionamide, ethoxylated $C_1-C_{26}$alkylamidopropyl lactobionamide, propoxylated $C_1-C_{26}$ alkylamidopropyl lactobionamide, ethoxylated/propoxylated $C_1-C_{26}$ alkylamidopropyl lactobionamide, $C_1-C_{26}$alkyl melibionamides, $C_1-C_{26}$ alkyl cellobionamides, $C_1-C_{26}$ alkyl gentiobionamides, $C_1-C_{26}$ alkyl glucopyranosyl-(1-5)-arabinonamides and the like.

Examples of heteroatom containing alkyl aldonamides suitable for this method include, but are not limited to $C_1-C_{26}$alkyloxypropyl glyceramide, $C_1-C_{26}$alkyloxypropyl ribonamide $C_1-C_{26}$ alkyloxypropyl gluconamide, $C_1-C_{26}$ alkyloxypropyl glucoheptonamide, $C_1-C_{26}$ alkyloxypropyldi(oxyethyl)gluconamide, $C_1-C_{26}$ alkyloxypropyltri(oxyethyl)gluconamide, $C_1-C_{26}$ alkyloxypropyltetra(oxyethyl)gluconamide, $C_1-C_{26}$ alkyloxypropylhepta(oxyethyl)gluconamide, $C_1-C_{26}$alkyloxypropylpoly(oxyethyl)gluconamide, $C_1-C_{26}$alkyloxypropylpoly(oxypropyl)gluconamide, $C_1-C_{26}$alkyloxypropylpoly(oxyethyl)poly(oxypropyl) gluconamide, $C_1-C_{26}$alkyloxypropyldi(oxyethyl) glucoheptonamide, $C_1-C_{26}$alkyloxypropyltri(oxyethyl) glucoheptonamide, $C_1-C_{18}$ alkyloxypropyltetra(oxyethyl) glucoheptonamide, $C_1-C_{26}$alkyloxypropylocta(oxyethyl) glucoheptonamide, $C_1-C_{26}$ alkyloxypropylpoly(oxyethyl) glucoheptonamide, $C_1-C_{26}$ alkyloxypropylpoly(oxypropyl) glucoheptonamide, $C_1-C_{26}$alkyloxypropylpoly(oxyethyl) poly(oxypropyl)glucoheptonamide, alkylpolyoxyethyl gluconamide, ethoxylated $C_1-C_{26}$alkyloxypropyl gluconamide, propoxylated $C_1-C_{26}$ alkyloxypropyl gluconamide, ethoxylated/propoxylated $C_1-C_{26}$ alkyloxypropyl gluconamide, propoxylated/ethoxylated $C_1-C_{26}$ alkyloxypropyl gluconamide, ethoxylated $C_1-C_{26}$ alkylamidopropyl gluconamide, propoxylated $C_1-C_{26}$ alkylamidopropyl gluconamide, ethoxylated/propoxylated $C_1-C_{26}$ alkylamidopropyl gluconamide, propoxylated/ethoxylated $C_1-C_{26}$ alkylamidopropyl gluconamide, $CH_1-C_{26}$ alkylsulfodioxidepropyl gluconamide $C_1-C_{26}$ alkyloxypropylaminopropyl gluconamide, $C_1-C_{26}$ alkyloxypropylamidopropyl gluconamide, $C_1-C_{18}$ alkyloxypropylamidopropyl glucoheptonamide, $C_1-C_{26}$ alkyloxypropylmethylamidopropylmethyl gluconamide, $C_1-C_{26}$alkyloxypropylamidopropylmethyl glucoheptonamide, gluconyl $C_1-C_{26}$alkyl glycinate and the like.

Examples of alkyl(glycosid)uronamides suitable for this method include, but are not limited to $C_1-C_{26}$alkylmethyl (methyl glucopyranosid)uronamide, $C_1-C_{26}$alkyl(ethyl glucopyranosid)uronamide, $C_1-C_{26}$alkyl(propyl galactopyranosid)uronamide, $C_1-C_{26}$alkyl(butyl galactofuranosid)uronamide, coconut(methyl glucofuranosid)uronamide, soya(glucopyranose)uronamide, tallow(galctofuranose)uronamide, castor(hydroxyethyl galactofuranosid)uronamide octadecenyl(methyl galactopyranosid)uronamide, linoleyl(ethyl glucofuranosid) uronamide, linolenyl(methyl glucofuranosid)uronamide, $C_1-C_{26}$ alkyloxypropyl(methyl glucofuranosid)uronamide, $C_1-C_{26}$ alkyloxypropylpoly[oxyethyl] (methylgalactopyranosid)uronamide, $C_1-C_{26}$alkyloxypropyl(amidoethyl)propyl(methyl glucopyranosid)uronamide, $C_1-C_{26}$ alkylglycinate(methyl glucofuranosid)uronamide, oleyl(methyl glucopyranosid) uronamide, tallow(glucopyranose)uronamide and the like Examples of sulfating agents suitable for this method include, but are not limited to chlorosulfonic acid, urea chlorosulfonic acid complex, sulfuric acid, urea sulfur acid complex, oleum, sulfamic acid, sulfur trioxide, dioxane sulfur trioxide complex and sulfur trioxide Lewis base complexes such as sulfur trioxide triethylamine complex, sulfur trioxide pyridine complex, sulfur trioxide urea complex and the like. Mixtures of sulfating agents can be used and may be preferred in certain cases.

Within the process of the invention, it is desirable to use water-free reaction components, but this not a necessary condition since low amounts of water (<0.5%) generally do not have a significant effect on the reaction. Also, within the process of the invention the sugar substrate can be added progressively to the sulfating agent, or the sulfating agent can be added progressively to the sugar substrate, preferably however, as seen in Examples 81–97, the sulfating agent is added progressively to the sugar substrate (dropwise) and in full amount at the beginning of the reaction. The degree of sulfation may be selected at will and is dependent on the molar ratio of sulfating agent to sugar substrate. Consequently, the sulfating agent can be used in stoichiometic (equal) molar amounts relative to the sugar substrate, or the sulfating agent can be used in molar deficiency or excess relative to the sugar substrate. Complete sulfation may not always be desirable and in some cases partial or modest sulfation is beneficial. In general, the molar ratio of sulfating agent to sugar substrate is from about 10:1 to about 1:10, preferably from about 8:1 to about 1:5, more preferably from about 5:1 to about 1:3, most preferably from about 2:1 to about 1:1.5. When a monosulfate adduct is prepared the molar ratio is from about 1.5:1 to about 1:1.5. Sulfation takes place almost exclusively on the primary hydroxyl group (at least 72–90% conversion) with small amounts of di/trisulfate and unsulfated starting material present. In addition, when unsaturation is present in the alkyl chain, the double bond may also be sulfated in minor amounts to form a sulfonate group. Double bond attack can be reduced by performing the sulfation in the presence of sodium chloride. These side products, when present in normal quantities, have little effect on the properties of the main product. When the sugar substrate is derived from a monosaccharide, a completely water soluble surfactant can be prepared by using the sulfating agent in a slight molar excess, preferably from about 1.5:1 to about 1.1:1. When the sugar substrate is derived from a disaccharide or larger, a completely water soluble surfactant can be prepared by using the sulfating agent in nearly stoichiometic molar amounts or less, preferably from about 1.3:1 to about 1:1.4. The monosulfated or partial sulfated adduct is generally preferred for detergent, personal product and oral hygiene applications and the di-, tri- and polysulfated adducts are generally preferred for personal product and pharmaceutical applications.

The sugar substrate is preferably in fine powder form, however solid, granular, flake, paste, syrup, gel or liquid form can be used as well. The sulfating agent is preferably in gaseous or liquid form, however solid, granular, flake, paste or gel form can be used as well.

The reaction can be preformed at or below room temperature, however the reaction may be also preformed at slightly elevated temperatures. Favorable reaction temperatures are from about −30° C. to about 100° C., preferably from about −20° C. to about 70° C., more preferably from about −10° C. to 50° C.

The reaction can be optionally carried out under pressure or reduced pressure to assist in the overall reaction rate, however, it is preferably carried out at atmospheric pressure and under an inert dry gas blanket (or bubbler) such as nitrogen, air, argon or helium. The inert gas stream is useful in maintaining a dry reaction environment, removing gaseous acids (e.g. such as hydrochloric acid obtained when using chlorosulfonic acid), excess volatile sulfating agent and certain low boiling solvents.

When gaseous sulfur trioxide is used the reaction is preferably done under atmospheric pressure.

After the reactants are added in full, they are mixed or stirred intensively for several hours, preferably from about 0.25 hour to about 24 hours, more preferably from about 0.5 hour to about 4 hours, most preferably when the reaction is complete and is varified by an analytical technique such as thin layer chromatography (TLC), infrared spectroscopy (IR), proton nuclear magnet resonance ($H^1$NMR), carbon 13 nuclear magnet resonance ($C^{13}$ NMR), mass spectrometry (MS), high pressure liquid chromatography (HPLC) and the like.

In general an organic solvent can be used to perform the reaction of the present invention, which should be sufficient to suspend or dissolve the sugar substrate and sulfating agent, but otherwise this is not essential condition. Typical levels of solvent used are from about 5% to about 98%, preferably from about 10% to about 70%, more preferably from about 15% to about 50% by weight of the total reaction mixture. Preferably the solvent is removed by known procedures such as simple distillation, vacuum distillation or rotaevaporation. When a low boiling solvent is used (b.p. <50° C.), it is preferably removed by blowing a dry inert gas stream below the solvent layer in the form of fine bubbles (e.g. nitrogen sparge).

In general, the anionic sugar based surfactants of the invention are isolated as solids (by gravity filtration, vacuum filtration, centrifugation, solvent removal or other separation techniques), however when syrups are obtained, crystallization may be enhanced by the addition of an organic solvent. The resulting product is subsequently filtered, washed with an organic solvent and air or vacuum dried.

Optionally, further purification of solid anionic sugar based surfactants of the invention can be perfromed by recrystallization in an organic solvent. The amount of solvent used is sufficient to dissolve the product, preferably with moderate heating. The solution is then slowly cooled until crystallization is complete, subsequently filtered, washed with an organic solvent and air or vacuum dried.

Still optionally, further purification of solid anionic sugar based surfactants of the invention can be preformed by column chromatography or by extraction techniques which are well known in the art.

Typical reaction solvents, crystallization solvents, recrystallization solvents and washing solvents that may be used include, but are not limited to acetic acid, acetone, acetonitrile, butanol, sec-butanol, tert-butanol, butyl acetate, butyl chloride, chloroform, cyclohexane, cyclopentane, dimethylformamide (DMF), dimethylacetamide, 2-ethoxyethanol, ethyl acetate, ethyl ether, ethylene glycol dimethyl ether(glyme), pentane, hexane, heptane, haxadecane, methanol, 2-methoxyethanol, 2-methoxyethyl acetate, methylethylketone (MEK), methylisoamylketone, methylisobutylketone, butylmethylketone, diisobutylketone, N-methyl-2-pyrrolidone, petroleum ether, propanol, isopropanol, propylene carbonate, pyridine, tetrachloroethylene, tetrahydrofuran (THF), tetramethylurea, toluene, trichloroethylene, 1,2,2-trichloro-1,2,2-trifluoroethane, 2,2,4-trimethylpentane, xylene, ethanol, pentyl acetate, carbon disulfide, 1-chlorobutane, 1,2-dichloroethane, 1,2-dimethoxyethane, glycerol, methylcyclohexane, ethylene glycol, furan, 1,2-dimethoxyethane, propylene glycol, 1-chloro-1,1-difluoroethane, isopropylbenzene(cumene), cyclohexanol, cyclohexanone, 4-hydroxy-4-methyl-2-pentanone(diacetone alcohol), water, diethylene glycol, diisopropyl ether, ethylene glycol monobutyl ether(2-butoxyethanol), hexylene glycol, isopentyl acetate, isobutyl acetate, isopropyl acetate, methyl acetate, methylpentylketone, dichloromethane, carbon tetrachloride, tetrachloroethylene, dichlorobenzene, ethylbenzene, diethylamine, triethylamine, trimethylamine, thioxane, sulfur dioxide and the like. Mixtures of solvents can be used as well and may be preferred in certain cases. Mixtures of solvents are useful in obtaining a desired polarity which may not be easily achieved through the use of individual solvents. Optimum polarity is most useful during crystallization and recrystallization. Preferred reaction solvents include halogenated solvents such as chloroform, 1-chlorobutane, 1,2-dichloroethane, dichloromethane, trichloroethylene, tetrachloroethylene, carbon tetrachloride, 1,2,2-trichloro-1,2,2-trifluoroethane, 1-chloro-1,1-difluoroethane; aromatic solvents such as toluene, xylene, dichlorobenzene, ethylbenzene, isopropylbenzene; nitrogen containing solvents such as dimethylformamide, dimethylacetamide, pyridine, diethylamine, triethylamine, trimethylamine as well as ether containing solvents such as ethyl ether, butyl ether, t-butyl methyl ether, petroleum ether, ethylene glycol dimethyl ether, tetrahydrofuran and thioxane. Preferred crystallization solvents, recrystallization solvents and washing solvents include alcoholic solvents such as methanol, ethanol, propanol, isopropanol, butanol, sec-butanol, tert-butanol, cyclohexanol and 2-ethoxyethanol; acetate solvents such as methyl acetate, ethyl acetate, butyl acetate, pentyl acetate, 2-methoxyethyl acetate, isopentyl acetate, isobutyl acetate and isopropyl acetate; hydrocarbon solvents such as cyclohexane, cyclopentane, pentane, hexane, heptane and haxadecane; as well as ketone containing solvents such as methylethylketone (MEK), methylisoamylketone, methylisobutylketone, butylmethylketone and diisobutylketone.

In certain cases it may be advantageous and more economical to perform the sulfation reaction in the absence of an organic solvent.

When a low boiling solvent is used (e.g. chloroform, methylene chloride, etc.) as a reaction solvent it is preferably removed by nitrogen sparge. The resulting paste may then be neutralized with base in water (or in an aqueous or non-aqueous solvent system) to a pH of about 4 to about 10, preferably from about 5 to about 9, more preferably from about 6 to about 8, followed by freeze drying, vacuum distillation, air drying or vacuum drying.

When water is used during neutralization, it may be more economical to leave it in with the final product thereby using it as a diluent making the product a pureable or pumpable liquid. Typical levels of water used as a diluent are from about 5% to about 95%, preferably from about 15% to about 70%, most preferably from about 20% to about 60% by weight of the total reaction mixture.

When an aqueous solvent system is used during neutralization, it may be more economical to leave it in with the final product thereby using the aqueous solvent system as a diluent making the product a pureable or pumpable liquid. Typical levels of aqueous solvent used as a diluent are from about 5% to about 95%, preferably from about 10% to about 80%, most preferably from about 15% to about 70% by weight of the total reaction mixture. Suitable solvents that may be mixed with water and used during neutralization are preferably methanol, ethanol, propanol, isopropanol, acetonitrile, acetone, propylene glycol, sorbitol, ethylene glycol, diethylene glycol, polyethylene glycol, glycerol, diglycerol, polyglycerol and the like. Most highly preferred diluent solvents are ethanol, isopropanol, propylene glycol, ethylene glycol, sorbitol, glycerol and mixtures thereof. Typical levels of solvent comprising the aqueous solvent system are from about 1% to about 70%, preferably from about 2% to about 45%, most preferably from about 3% to about 35% by weight of the total aqueous solvent system.

When a non-aqueous solvent system is used (solvent only) during neutralization, the product can be sometimes isolated as a solid (by filtration) which can be washed with an organic solvent and then air or vacuum dried.

Examples of suitable bases that may be used to neutralize sulfated alkyl aldobionamides, sulfated heteroatom containing alkyl aldonamides and sulfated alkyl(glycosid) uronamides of the invention include, but are not limited to sodium hydroxide, potassium hydroxide, sodium carbonate, sodium bicarbonate, ammonium hydroxide, magnesium hydroxide, lithium hydroxide, calcium hydroxide, sodium methoxide, sodium ethoxide, ammonia, monoethanolamine, diethanolamine, triethanolamine, methylamine, dimethylamine, triethylamine, methyl glucamine, glucamine, chitosamine(glucosamine), 2-amino-2-ethyl-1-3-propanediol, tris(hydroxymethyl)aminomethane, sodium glycinate, potassium glycinate, ammonium glycinate, sodium alaninate, sodium lysinate, potassium lysinate, sodium methioninate, sodium prolinate, sodium serinate, sodium asparaginate, sodium glutaminate, 1-amino-2-propanol, 2-amino-2-methylpropanol, tris(hydroxyethyl) amine, 3-amino-1,3-propanediol, 3-methylamino-1,3-propanediol and the like as well as mixtures thereof.

Bleaching is sometimes required but not always necessary since the compounds of the invention are generally of good color. Bleaching agents or hydrogen peroxide liberating or generating compounds that may be used to further improve product color include, but are not limited to hydrogen peroxide, sodium hypochlorite, potassium hypochlorite, calcium hpochlorite, lithium hypochlorite, dibasic magnesium hypochlorite, sodium hypobromite, chlorinated trisodium phosphate, hypochlorous acid, chlorine dioxide, sodium perborate, sodium percarbonate, potassium percarbonate, oxone, t-butyl hydroperoxide, benzoylperoxide, bis (trimethylsilyl)peroxide, peroxymonosulfate, peroxyformic acid, peroxyacetic acid, peroxytrifluoroacetic acid, peroxybenzoic acid, m-chloroperoxybenzoic acid, peroxyphthalic acid, peroxypropionic acid, peroxypropionic acid, peperoxylauric acid and the like. A preferred bleaching agent is hydrogen peroxide. Bleaching may be done in water or in an inert organic solvent, preferably after neutralization at about 0° C. to about 50° C. Typical levels of bleaching agent are from about 0.01% to about 7%, preferably from about 0.02% to about 5%, most preferably from about 0.03% to about 3% by weight of the total reaction mixture.

Product color improvement may also be carried out by using reducing agents belonging to two classes:

The first class of agents comprises compounds which include sulfur in the +4 oxidation state and show a negative oxidation relative to hydrogen. Illustrative of this class are the salts of sulfite, bisulfite, hydrosulfite (dithionite), metabisulfite (pyrosulfite) and mixtures thereof. Suitable salt counterions include alkali metal, alkaline earth metal, ammonium, alkyl- or hydroxyalkyl ammonium cations and mixtures thereof.

Specific examples of sulfur compounds in the +4 oxidation state useful as reducing agents include, but are not limited to sodium sulfite, potassium sulfite, calcium sulfite, sodium bisulfite (sodium hydrogen sulfite), potassium bisulfite, sodium hydrosulfite, zinc hydrosulfite, sodium metabisulfite, potassium metabisulfite and the like. Sulfur dioxide, sulfurous acid and sodium sulfoxylate formadehyde are useful as well.

The second class of reducing agents includes those compounds having hydrogen in the −1 oxidation state and show a negative oxidation potential relative to hydrogen. Illustrative of this class are sodium hydride, potassium hydride, lithium hydride, magnesium hydride, calcium hydride, sodium borohydride, sodium cyanoborohydride, lithium borohydride, potassium borohydride, magnesium borohydride, alkyl- and alkoxy borohydrides, diborane, sodium aluminum hydride, potassium aluminum hydride, calcium aluminum hydride, lithium aluminum hydride, alkyl- and alkoxyaluminum hydrides such as dihydrobis(2-methoxyethoxy)aluminate and mixtures thereof. Particularly preferred among the foregoing are the boron hydrides, most especially preferred are sodium bisulfite, sodium borohydride and mixtures thereof. Reduction may be done in water or in an inert organic solvent, preferably after neutralization at about 0° C. to about 50° C. Typical levels of reducing agent are from about 0.01% to about 7%, preferably from about 0.02% to about 5%, most preferably from about 0.03% to about 3% by weight of the total reaction mixture.

It has been further found that use of color improvement agents (bleaching or reducing agent) produces anionic sugar based surfactants having improved color. Compounds treated in this manner are isolated as stable white crystalline solids and form clear water white solutions.

It has also been shown that treated anionic sugar based surfactants of the invention remain of good color at room temperature for more than 24 months.

Essential Steps of The Sulfation Process

The essential steps of the process for manufacturing a sulfated sugar based anionic surfactant selected from the group consisting of sulfated alkyl aldobionamides, sulfated heteroatom containing alkyl aldonamides or sulfated alkyl (glycosid)uronamides comprises the steps of:
(1) preparing a heterogeneous suspension or homogeneous solution comprising of a mixture of alkyl aldobionamide, heteroatom containing alkyl aldonamide or alkyl (glycosid)uronamide and organic solvent;
(2) adding a sulfating agent to said polyhydroxyamide suspension or solution such that the molar ratio of sulfating agent to polyhydroxyamide is from about 10:1 to about 1:10;
(3) optionally heating the mixture of sulfating agent and polyhydroxyamide suspension or solution to a temperature from about −30° C. to about 100° C.;
(4) allowing the sulfating agent and polyhydroxyamide suspension or solution to react under rapid agitation until deemed complete;
(5) optionally removing the organic solvent by distillation or inert gaseous sparge;
(6) optionally adding water or an aqueous solvent system and neutralizing the resulting sulfated alkyl aldobionamide, sulfated heteroatom containing alkyl aldonamide or sulfated alkyl(glycosid)uronamide with base followed by optional treatment with a bleaching or reducing agent at a temperature from about from about 0° C. to about 50° C.;
(7) removing the solvent by distillation or allowing the water to remain with the finished product for use as a diluent.

The Sulfation Reaction

It is should be generally understood that the anionic sugar based surfactants of the present invention are believed to consist mainly of monosulfates attached to the primary hydroxy group of the polyhydroxyamide substrate. However, since the compounds of the invention contain multiple hydroxy groups di-, tri-, tetra- etc. and polysulfates can be formed in varying amounts. In addition, sodium sulfate may be present in minor amounts (<0.5–6%) which is caused by the hydrolysis of the sulfate group or the hydrolysis of any unreacted sulfating agent that may be present during the neutralization step. Furthermore, sodium chloride may also be present in minor amounts (<0.5–1.5%) which is caused by the hydrolysis of chlorosulfonic acid or hydrochloric acid during the neutralization step. The presence of these minor ingredients can routinely occur and do not detract from the performace herein, and no special purification steps are required to removed them.

Home Application and Use

The anionic sugar based surfactants of the present invention are useful in detergent, personal product, oral hygiene, food and pharmacological compositions which are available in a variety of types and forms. Preferred applications are detergent, personal product and oral hygiene compositions.

A classification according to detergent type would consist of heavy-duty detergent powders, heavy-duty detergent liquids, light-duty liquids (dishwashing liquids), institutional detergents, specialty detergent powders, specialty detergent liquids, laundry aids, pretreatment aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair promade products, brilliantines and the like.

Examples bath products include, but are not limited to bath oils, foam or bubble bathes, therapeutic bathes, after bath products, after bath splash products and the like.

Examples cleansing products include, but are not limited to shower cleansers, shower gels, body shampoos, hand/body/facial cleansers, abrasive scrub cleansing products, astringent cleansers, makeup cleansers, liquid soaps, toilet soap bars, syndet bars and the like.

Examples skin care products include, but are not limited to hand/body/facial moisturizers, hand/body/facial creams, massage creams, hand/body/facial lotions, sunscreen products, tanning products, self-tanning products, aftersun products, masking products, lipsticks, lip gloss products, rejuvenating products, antiaging products, antiwrinkle products, anticellulite products, antiacne products and the like.

Examples shaving products include, but are not limited to shaving creams, aftershave products, preshave products and the like.

Examples deodorant/antiperspirant products include, but are not limited to deodorant products, antiperspirant products and the like.

A classification according to oral hygiene type would consist of, but is not limited to mouthwashes, pre-brushing dental rinses, post-bushing rinses, dental sprays, dental creams, toothpastes, toothpaste gels, toothpowders, dental cleansers, dental flosses, chewing gums, lozenges and the like.

The anionic sugar based surfactants of the present invention are also useful in softening compositions such as liquid fabric softeners, fabric softening rinses, fabric softening sheets, tissue papers, paper towels, facial tissues, sanitary tissues, toilet paper and the like.

A classification according to detergent, personal product and oral hygiene form would consist of aerosols, liquids, gels, creams, lotions, sprays, pastes, roll-on, stick, tablet, powdered and bar form.

A comprehensive list of essential and optional ingredients that are useful in detergent, personal product and oral hygiene compositions are described in McCutcheon's, Detergents and Emulsifiers (Vol 1) and McCutcheon's, Functional Materials (Vol 2), 1992 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference. Typical levels of anionic sugar based surfactant are from about 0.001% to about 100%, preferably from about 0.01% to about 80%, more preferably from about 0.05% to about 60%, most preferably from about 0.1% to about 50% by weight of the total composition.

Industrial Application and Use

The anionic sugar based surfactants of the present invention are useful as mild anionic surfactants that may be used alone or in combination with other surfactants to provide improved foam and clarity. More specifically, the anionic sugar based surfactants of the invention are useful as sole surfactants, cosurfactants, detergents, detergency enhancing agents, foaming agents, foam stabilizing/boosting agents, wetting agents, solubilizing agents, lime soap dispersants, anti-hygroscopic agents, flow agents, processing aids, softening agents moisturizers, skin (cell) proliferation agents and the like. In fact, by simple experimentation, which are well known to those skilled in the art, unique synergies of anionic sugar based surfactants with essential and optional ingredients can be obtained and determined.

Modified Anionic Sugar Based Surfactants For Detergent Applications

The anionic sugar based surfactants of the present invention can be modified for use in detergent formulations. Under some circumstances, the formulator of a detergent composition may find it desirable to provide low foam during the washing process. For example, low foaming compositions are desirable for window cleaners, floor cleaners, wall cleaners and other hard surface cleansers where excess foaming would require additional inconvenient rinsing steps in the overall cleaning process. Also, dishwashing detergents for use in automatic dishwashing machines must also be formulated to have essentially no foam, since excess foam can actually spill out of such machines which is an undesirable trait. Likewise, in European-style front loading fabric washing machines, detergent compositions must be formulated to provide low foam which will avoid such suds spillage. The compounds of the invention are generally high foaming, however, anionic sugar based surfactants where $R_1$ is $C_3$–$C_8$ are believed to be more low foaming, whereas anionic sugar based surfactants where $R_1$ is hydrogen (H) or $C_1$–$C_2$ are believed to be more high foaming. In any event, the foam of a detergent composition can be easily controlled by proper selection of the correct suds control agent. Examples of such agents include, but are not limited to $C_{10}$–$C_{24}$ fatty acids and their salts, high molecular weight hydrocarbons (e.g. paraffins), fatty acid esters (e.g. fatty acid triglycerides), $C_{18}$–$C_{40}$ ketones, hydrocarbons, silcone sud suppressing agents and the like. A more complete list of various suds control agent are given in Kirk Othmer Encyclopedia of Chemical Technology, Third Edition, Volume 7, pages 430–447, (John Wiley & Sons, Inc. 1979) which is incorporated herein by reference.

It should be understood that anionic sugar based surfactants of the present invention are conventionally prepared in their acid or alkali metal, ammonium, alkanolammonium etc. forms. However, under certain circumstances where high grease and oily soil removal performace is of importance, the formulator may find it advantageous to incorporate at least about 0.5%, preferably from about 0.6% to about 2% by weight of magnesium and/or calcium counterions, into the finished detergent formulation. This can be done by adding various water soluble salts such as chlorides, sulfates, acetates etc. of magnesium or calcium to the detergent composition. It is also useful to generate the magnesium and/or calcium salts of the anionic sugar based surfactants of the invention by reacting magnesium hydroxide or calcium hydroxide with the acid form which can be conveniently done in situ during the formulation of the finished detergent composition or as a separate step during the manufacture of the anionic sugar based surfactant.

Methodology

Analysis of (Non-Sulfated) Monosaccharide Aldonamides by Gas Chromatography

Gas chromatography was found to be a convenient method for the examination of monosaccharide alkyl aldonamides, heteroatom containing alkyl aldonamides and alkyl(glycosid)uronamides of the present invention. The method of persilylation with hexamethyldisilazane (HMDS) and trimethylchlorosilane (TMCS) in pyridine is the simplest way for producing sufficiently stable and volatile derivatives for analysis. The mixture of both agents are more reactive than either reagent alone, and the by-products combine to form neutral ammonium chloride ($NH_4Cl$) or pyridine hydrochloride ($C_5H_5N$ HCl).

The purity of several monosaccharide aldonamides and uronamides were determined and found to be 97–99.9%. All products were well separated from starting materials, however aldonamides with alkyl chains containing eighteen carbons or more were not volatile enough for analysis.

Approximately 7–10 mg of a monosaccharide aldonamide and uronamide compounds were treated with 1 ml of sil-prep reagent (pyridine:HMDS:TMCS=9:3:1) in a 1 dram stoppered vial containing a magnetic stirring bar. The mixture was stirred vigorously at room temperature for about a hour or longer prior to chromatography. The solution became cloudy owing to precipitation of $NH_4Cl$ and $C_5H_5N$ HCl which was filtered through a CAMEO II 25 mm filter. From about 1.0 μl to about 1.1 μl of the resulting mixture was injected into the gas chromatograph.

All gas chromatography was conducted on a Hewlett Packard 5890 Series II Gas Chromatograph. All sample components were detected by a flame ionization detector using a split ratio of 100:1 and separated on a crosslinked 5% phenylmethyl silicone capillary column 25 m×0.32 mm×0.53 μm. The carrier gas was helium at 1 ml/minute and the temperature program was 3 minutes at 140° C. then 30° C./minute to 250° C. for 75 minutes.

EXAMPLES

The following Examples further describe and demonstrate the preferred embodiments that are within the scope of the present invention. The Examples are given solely for the purpose of illustration and are not to be construed as being limiting to the present invention since many variations are possible without departing from the spirit and scope of the invention. For instance, Examples 1–46 describe the preparation of alkyl aldonamides and heteroatom containing alkyl aldonamides. Examples 47 to 74 describe the preparation alkyl aldobionamides and heteroatom containing alkyl aldonamides. Examples 75 to 79 describe the preparation of alkyl(glycosid)uronamides and heteroatom containing alkyl (glycosid)uronamides. Several of the above Examples (polyhydroxyamide nonionic surfactants) are used as substrates which are converted into the corresponding anionic sugar based surfactant. Examples 81 to 86 are comparative and Examples 87 to 102 are of the invention.

Example 1

(No Heteroatom)

Preparation of Dodecyl D-Ribonamide

A 200 ml four necked round bottom flask equipped with a condenser, addition funnel, thermometer and mechanical stirrer was charged with D-ribono-1,4-lactone (15.0 g, 0.10 mole) and methanol (45 g, for 43% total solids). The suspension was heated to 40°–43° C. for 15 minutes and the heating mantle removed. Dodecylamine (18.8 g, 0.10 mole) containing methanol (5 ml) was added dropwise over ½ hour. The reaction mixture was allowed to cool to room temperature (about 21° C.) followed by stirring overnight to allow complete crystallization. The white product was filtered, washed with methanol (3×20 ml) and dried under vacuum at 40°–45° C. giving 31.5 g (93% yield) of dodecyl D-ribonamide with a melting point of 101°–102° C. and 99.9% purity.

Example 2

(No Heteroatom)

Preparation of Coco D-Gluconamide

A 5 liter four necked round bottom flask equipped with a condenser, addition funnel, thermometer and mechanical stirrer was charged with D-glucono-1,5-lactone (480.0 g, 2.69 moles) and methanol (2752 g, for 27% total solids). The suspension was heated to 40°–50° C. for 15 minutes and the heating mantle removed. Cocoamine (538.0 g, 2.69 moles) containing methanol (80 ml) was added dropwise over ½ hour. The reaction mixture was allowed to cool to room temperature (about 21° C.) followed by stirring overnight to allow complete crystallization. The white product was filtered, washed with methanol (3×500 ml) and dried under vacuum at 40°–45° C. giving 947.0 g (93% yield) of coco D-gluconamide with a melting point of 147°–148° C.

Examples 3–20

(No Heteroatom)

The monosaccharide alkyl aldonamides (Examples 3–20) in Table 1 were prepared in a similar manner as in Example 2.

TABLE 1

Monosaccharide Alkyl Aldonamides

| Example | Compound | Attached Hydrocarbon | MP (°C.) | % Yield | % Purity (GC) |
|---|---|---|---|---|---|
| 3 | D-Gluconamide | $C_7H_{15}$ | 159–160 | 93 | 99.7 |
| 4 | D-Gluconamide | $C_8H_{17}$ | 159–160 | 90 | 99.9 |
| 5 | D-Gluconamide | $C_9H_{19}$ | 158–159 | 92 | 99.9 |
| 6 | D-Gluconamide | $C_{10}H_{21}$ | 157–158 | 91 | 99.9 |
| 7 | D-Gluconamide | $C_{11}H_{23}$ | 156–157 | 92 | 99.9 |
| 8 | D-Gluconamide | $C_{12}H_{25}$ | 155–156 | 96 | 99.9 |
| 9 | L-Gluconamide | $C_{12}H_{25}$ | 154–155 | 95 | 99.9 |
| 10 | D-Gluconamide | $C_{13}H_{27}$ | 155–156 | 95 | 99.9 |
| 11 | D-Gluconamide | $C_{14}H_{29}$ | 154–155 | 92 | 97.4 |
| 12 | D-Gluconamide | $C_{16}H_{33}$ | 152–153 | 94 | 99.9 |
| 13 | D-Gluconamide | $C_{18}H_{37}$ | 147–149 | 94 | — |
| 14 | D-Gluconamide | Tallow | 141–142 | 91 | — |
| 15 | D-Gluconamide | Soya | 135–137 | 86 | — |
| 16 | D-Gluconamide | Oleyl | 130–131 | 86 | — |

TABLE 1-continued

Monosaccharide Alkyl Aldonamides

| Example | Compound | Attached Hydrocarbon | MP (°C.) | % Yield | % Purity (GC) |
|---|---|---|---|---|---|
| 17 | D-Galactonamide | $C_{12}H_{25}$ | 187–188(d) | 93 | 99.8 |
| 18 | L-Galactonamide | $C_{12}H_{25}$ | 187–188(d) | 95 | 99.7 |
| 19 | L-Mannonamide | $C_{12}H_{25}$ | 159–160 | 95 | 90.6 |
| 20 | D-Glycero-L-Mannoheptonamide | $C_{12}H_{25}$ | 195–197(d) | 97 | 98.6 | d = decomposition occurred during melting.

Example 23

(1 Ether Heteroatom)

Preparation of Octyl/Decyloxypropyl D-Ribonamide

A 250 ml four necked round bottom flask equipped with a condenser, additional funnel, thermometer and mechanical stirrer was charged with ribono-1,4-lactone (10.0 g, 0.07 mole) and methanol (37 g for 40% total solids). The suspension was heated to 40°–50° C. for 15 minutes and heating mantle removed. Octyl/decyloxypropylamine (14.6 g, 0.07 mole) was added dropwise over ½ hour and the reaction mixture stirred for six hours. The white product was filtered, washed with cold acetone (3×10 ml) and dried under vacuum at 40°–45° C. giving 14.0 g (57% yield) of octyl/decyloxypropyl D-ribonamide with a melting point of 71°–72° C. and 98.7% purity (62.8%/35.9%:$C_8/C_{10}$).

Examples 24–34

(1 Ether Heteroatom)

The monosaccharide alkyloxypropyl aldonamides (Examples 24–34) in Table 2 were prepared in a similar manner as in Example 23.

panol was added and the product was recrystallized, filtered, washed with cold isopropanol (3×5 ml) and dried under vacuum at 40°–45° C. giving 3.4 g (29% yield) of octyl/decyloxypropyl D-glyceramide.

Example 36

(1 Ester Heteroatom)

Preparation of N-D-Gluconyl Dodecyl Glycinate

A 100 ml round bottom flask equipped with a condenser, addition funnel, thermometer and mechanical stirrer was charged with D-glucono-1,5-lactone (5.0 g, 0.03 mole) and isopropanol (35 g). The suspension was heated to 50° C. over 15 minutes. A mixture of glycine dodecyl ester p-toluenesulfonate salt (11.7 g, 0.03 mole), triethylamine (2.9 g 0.03 mole) and isopropanol (20 g) were added dropwise over 15 minutes from an addition funnel. The reaction mixture was stirred rapidly for about 2 hrs and then cooled to room temperature. The white product was filtered, washed with chloroform (3×150 ml) and dried under high vacuum at 35° C. giving 7.2 g (61% yield) of N-D-gluconyl dodecyl glycinate with a melting point of 121°–122° C. and 98.6% purity.

TABLE 2

Monosaccharide Alkyloxypropyl Aldonamides

| Example | Compound | Attached Hydrocarbon | MP (°C.) | % Yield | % Purity (GC) |
|---|---|---|---|---|---|
| 24 | D-Gluconamide | $C_3H_6OCH_2CH(C_2H_5)C_4H_9$ | 80–90 | 73 | 99.9 |
| 25 | D-Gluconamide | $C_3H_6OC_8H_{17}/C_{10}H_{21}$ | 119–120 | 83 | 63.7/35.6 |
| 26 | D-Gluconamide | $C_3H_6O$-Isodecyl | 96–101 | 83 | — |
| 27 | D-Gluconamide | $C_3H_6OC_{12}H_{25}$ | 129–130 | 96 | 99.5 |
| 28 | D-Gluconamide | $C_3H_6O$-Isotridecyl | 81–86 | 74 | — |
| 29 | D-Gluconamide | $C_3H_6OC_{12}H_{25}$ to $C_{15}H_{31}$ | 125–126 | 82 | — |
| 30 | D-Gluconamide | $C_3H_6OC_{14}H_{29}$ | 129–130 | 86 | 99.7 |
| 31 | D-Glucoheptonamide | $C_3H_6OC_8H_{17}/C_{10}H_{21}$ | 129–130 | 88 | 66.2/33.6 |
| 32 | D-Glucoheptonamide | $C_3H_6O$-Isodecyl | 100–105 | 85 | — |
| 33 | D-Glucoheptonamide | $C_3H_6OC_{12}H_{25}$ | 133–134 | 89 | 99.9 |
| 34 | D-Glucoheptonamide | $C_3H_6OC_{12}H_{25}$ to $C_{15}H_{31}$ | 128–129 | 75 | — |

Example 35

(1 Ether Heteroatom)

Preparation of Octyl/Decyloxypropyl D-Glyceramide (No Solvent)

A 50 ml four necked round bottom flask equipped with a condenser, additional funnel, thermometer and mechanical stirrer was charged with methyl glycerate (5.1 g, 0.04 mole) and octyl/decyloxypropylamine (8.0 g, 0.04 mole). The reaction mixture was heated to 65° C. for 24 hours. Isopro-

Example 37

(1 Ester Heteroatom)

Preparation of N-D-Gluconyl Dodecyl Ester of Ethanolamine

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 65° C. over 15 minutes. A mixture of dodecyl ester of monoethanolamine p-toluenesulfonate salt (16.3 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 13.3 g (81% yield) of N-D-gluconyl dodecyl ester of ethanolamine with a melting point of 142°–143° C. and 97.4% purity.

Example 38

(1 Ester Heteroatom)

Preparation of N-D-Gluconyl Dodecyl DL-Alaninate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of DL-alanine dodecyl ester p-toluenesulfonate salt (16.9 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 12.5 g (73% yield) of N-D-gluconyl dodecyl alaninate with a melting point of 97°–98° C. and 98.8% purity.

Example 39

(1 Ester and 2 Ether Heteroatoms)

Preparation of N-D-Gluconyl Dodecyldi(oxyethyl) Glycinate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of glycine dodecyldi(oxyethyl) ester p-toluenesulfonate salt (20.2 g, 0.04 mole), triethylamine (4.0 g 0.04 mole) and isopropanol (20 g) were added dropwise over 15 minutes from an addition funnel. The reaction mixture was stirred rapidly for about 8 hrs and then cooled to room temperature. The white product was filtered, washed with chloroform (3×150 ml) and dried under high vacuum at 35° C. giving 8.9 g (43% yield) of N-D-gluconyl dodecyldi(oxyethyl)glycinate.

Example 40

(1 Amino Heteroatom)

Preparation of Cocoaminopropyl D-Gluconamide

A 1 liter round bottom flask equipped with a condenser, addition funnel, thermometer and mechanical stirrer was charged with D-glucono-1,5-lactone (100.0 g, 0.56 mole) and methanol (208 g for 55% total solids). The suspension was heated to 40° C. over 15 minutes and the heating mantle removed. Cocoaminopropylamine (153.8 g, 0.56 mole) was added dropwise over 15 minutes with rapid stirring. The reaction mixture was cooled and placed in a refrigerator at 0° C. overnight. The white product was filtered, washed with cold isopropanol (3×100 ml) and dried under high vacuum at 35° C. giving 206.0 g (81% yield) of cocoaminopropyl D-gluconamide with a melting point of 109°–111° C.

Example 41

(1 Amino Heteroatom)

Preparation of Hydrogenated Tallowaminopropyl D-Gluconamide

A 1 liter round bottom flask equipped with a condenser, addition funnel, thermometer and mechanical stirrer was charged with D-glucono-1,5-lactone (20.0 g, 0.11 mole) and methanol (56 g). The suspension was heated to 40° C. over 15 minutes and the heating mantle removed. Hydrogenated tallowaminopropylamine (36.0 g, 0.11 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (83% yield) of hydrogenated tallowaminopropyl D-gluconamide with a melting point of 112°–115° C.

Example 42

(1 Amino Heteroatom)

Preparation of Soyaaminopropyl D-Gluconamide

A 100 ml round bottom flask equipped with a condenser, addition funnel, thermometer and mechanical stirrer was charged with D-glucono-1,5-lactone (5.4 g, 0.03 mole) and methanol (7 g). The suspension was heated to 40° C. over 15 minutes and the heating mantle removed. Soyaaminopropylamine (10.0 g, 0.03 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 14.1 g (92% yield) of soyaaminopropyl D-gluconamide with a melting point of 97°–100° C.

Example 43

(1 Amino Heteroatom)

Preparation of Oleylaminopropyl D-Gluconamide

A 500 ml round bottom flask equipped with a condenser, addition funnel, thermometer and mechanical stirrer was charged with D-glucono-1,5-lactone (25.0 g, 0.14 mole) and methanol (31 g). The suspension was heated to 40° C. over 15 minutes and the heating mantle removed. Oleylaminopropylamine (47.7 g, 0.14 mole) was added dropwise over 10 minutes and the reaction stirred for 6 hours. Acetone (300 ml) was added and the flask placed in a refrigerator overnight. The white solid was filtered, washed with cold acetone (3×50 g) and dried under vacuum at 35° C. giving 65.0 g (89% yield) of oleylaminopropyl D-gluconamide with a melting point of 100° C.–103° C.

Examples 44–45

(1 Amino and 1 Ether Heteroatom)

The monosaccharide alkyloxypropylaminopropyl aldonamides (Examples 44–45) in Table 3 were prepared in a similar manner as in Example 43.

TABLE 3

Monosaccharide Alkyloxypropylaminopropyl Aldonamides

| Example | Compound | Attached Hydrocarbon | MP (°C.) | % Yield | % Purity (GC) |
|---|---|---|---|---|---|
| 44 | D-Gluconamide | $C_3H_6NHC_3H_6O$-Isotridecyl | 89–90 | 70–77 | — |
| 45 | D-Gluconamide | $C_3H_6NHC_3H_6OC_{12}H_{25}$ to $C_{15}H_{31}$ | 119–120 | 91–95 | — |

Example 46

(1 Amide Heteroatom)

Preparation of Hexylamido-2-Methylpentyl D-Gluconamide and Hexylamido-4-Methylpentyl D-Gluconamide A 100 ml round bottom flask equipped with a condenser, addition funnel, thermometer and mechanical stirrer was charged with D-glucono-1,5-lactone (6.7 g, 0.04 mole) and isopropanol (35 g). The suspension was heated to 50° C. over 25 minutes and the heating mantle removed. A mixture of hexylamido-2-methylpentylamine and hexylamido-4-methylpentylamine (45%/55%, 8.0 g, 0.04 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 7.6 g (52% yield) of hexylamido-2-methylpentyl D-gluconamide and hexylamido-4-methylpentyl D-gluconamide.

Example 47

(No Heteroatom)

Preparation of Nonyl D-Lactobionamide

A 100 ml round bottom flask equipped with a condenser, addition funnel, thermometer and mechanical stirrer was charged with D-lacto-biono-1,5-lactone (100.0 g, 0.29 mole) and methanol (300 g). The suspension was heated to 50° C. over 15 minutes. Nonylamine (39.1 g, 0.27 mole) was added dropwise over 15 minutes with rapid stirring. The reaction mixture was cooled to room temperature and stirred overnight. The product was filtered, washed with cold methanol (1×100 ml) and dried under vacuum at 35° C. The product was then recrystallized in methanol giving 110.0 g (84% yield) of nonyl D-lactobionamide with a melting point of 149°–150° C.

Examples 48–61

(No Heteroatom)

The disaccharide alkyl aldonamides (Examples 48–61) in Table 4 were prepared in a similar manner as in Example 47.

TABLE 4

Dosaccharide Alkyl Aldobionamides

| Example | Compound | Attached Hydrocarbon | MP (°C.) | % Yield | % Purity (GC) |
|---|---|---|---|---|---|
| 48 | D-Lactobionamide | $C_{10}H_{21}$ | 138–139 | 47 | 99.0 |
| 49 | D-Lactobionamide | $C_{11}H_{23}$ | 147–148 | 34 | 99.2 |
| 50 | D-Lactobionamide | $C_{12}H_{25}$ | 137–138 | 35 | 99.3 |
| 51 | D-Lactobionamide | $C_{13}H_{27}$ | 147–148 | 36 | 99.9 |
| 52 | D-Lactobionamide | $C_{14}H_{29}$ | 126–127 | 92 | 97.4 |
| 53 | D-Lactobionamide | $C_{15}H_{31}$ | 147–148 | 70 | 99.3 |
| 54 | D-Lactobionamide | $C_{16}H_{33}$ | 130–131 | 60 | 99.3 |
| 55 | D-Lactobionamide | $C_{18}H_{37}$ | 112–113 | 92 | — |
| 56 | D-Lactobionamide | Tallow | 109–111 | 65 | 97.5 |
| 57 | D-Lactobionamide | Oleyl | 104–106 | 71 | — |
| 58 | D-Maltobionamide | $C_{11}H_{23}$ | 109–110 | 26 | 99.7 |
| 59 | D-Maltobionamide | $C_{12}H_{25}$ | 114–115 | 26 | 99.7 |
| 60 | D-Maltobionamide | $C_{14}H_{29}$ | 118–119 | 31 | 99.7 |
| 61 | D-Maltobionamide | $C_{16}H_{33}$ | 122–123 | 67 | 98.0 |

Example 62

(1 Ether Heteroatom)

Preparation of Octyl/Decyloxypropyl D-Lactobionamide

A 2 liter round bottom flask equipped with a condenser, addition funnel, thermometer and mechanical stirrer was charged with D-lactobion-1,5-lactone (84.1 g, 0.25 mole), methanol (250 g for 35% total solids) and methanesulfonic acid (3 drops). The suspension was heated to 50° C. over 15 minutes and the heating mantle removed. Octyl/decyloxypropylamine (50.0 g, 0.25 mole) was added dropwise over 15 minutes with rapid stirring. The reaction mixture was cooled and stirred at room temperature overnight with 30% hydrogen peroxide (1 ml). Methanol was removed by vacuum distillation and acetone (1000 ml) added. The white product was filtered, washed with cold acetone (3×250 ml) and dried under high vacuum at 35° C. giving 112.2 g (84% yield) of octyl/decyloxypropyl D-lactobionamide with a melting point of 99°–101° C.

Example 63

(1 Ether Heteroatom)

Preparation of Dodecyloxypropyl D-Lactobionamide

A 3 liter round bottom flask equipped with a condenser, addition funnel, thermometer and mechanical stirrer was charged with D-lactobiono-1,5-lactone (180.0 g, 0.53 mole) and methanol (1100 ml). The suspension was heated to 50° C. over 15 minutes and the heating mantle removed. Dodecyloxypropylamine (128.8 g, 0.53 mole) was added dropwise over 30 minutes with rapid stirring. The reaction mixture was cooled and stirred at room temperature overnight. The white product was filtered, washed with cold acetone (2×400 ml) and dried under high vacuum at 40° C. giving 224.5 g (73% yield) of dodecyloxypropyl D-lactobionamide with a melting point of 117°–118° C.

Example 64

(1 Ether Heteroatom)

Preparation of Dodecyloxypropyl D-Maltobionamide

A 100 ml round bottom flask equipped with a condenser, addition funnel, thermometer and mechanical stirrer was charged with D-maltobiono-1,5-lactone (6.0 g, 0.02 mole) and methanol (25 ml). The suspension was heated to 50° C. over 15 minutes and the heating mantle removed. Dodecyloxypropylamine (4.3 g, 0.02 mole) was added dropwise over 30 minutes with rapid stirring. Acetone (50 ml) was added and the reaction mixture stirred at room temperature overnight. The white product was filtered, washed with cold acetone (3×30 ml) and dried under high vacuum at 30° C. giving 5.9 g (57% yield) of dodecyloxypropyl D-maltobionamide.

Example 65

(1 Ether Heteroatom)

Preparation of Dodecyl to Pentadecyloxypropyl D-Lactobionamide

A 2 liter round bottom flask equipped with a condenser, addition funnel, thermometer and mechanical stirrer was charged with D-lactobion-1,5-lactone (65.2 g, 0.19 mole), methanol (214 g for 30% total solids) and methanesulfonic acid (3 drops). The suspension was heated to 50° C. over 15 minutes and the heating mantle removed. Dodecyl to pentadecyloxypropylamine (50.0 g, 0.19 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 98.7 g (86% yield) of dodecyl to pentadecyloxypropyl D-lactobionamide with a melting point of 95°–98° C.

Example 66

(1 Ether Heteroatom)

Preparation of Tetradecyloxypropyl D-Lactobionamide

A 5 liter round bottom flask equipped with a condenser, addition funnel, thermometer and mechanical stirrer was charged with D-lacto-biono-1,5-lactone (500.0 g, 1.47 moles) and methanol (3000 ml). The suspension was heated to 50° C. over 30 minutes and the heating mantle removed. Tetradecyloxypropylamine (401.7 g, 1.47 mole) was added dropwise over 30 minutes with rapid stirring. The reaction mixture was cooled and stirred at room temperature overnight. The white product was filtered, washed with cold acetone (2×700 ml) and dried under high vacuum at 40° C. giving 656.1 g (73% yield) of tetradecyloxypropyl D-lactobionamide.

Example 67

(1 Ester Heteroatom)

Preparation of N-D-Lactobionyl Dodecyl Glycinate

A 50 ml round bottom flask equipped with a condenser, thermometer and mechanical stirrer was charged with dodecyl glycinate hydrochloride (9.0 g, 0.03 mole) and 2.0M methanolic ammonia (16 ml, 0.03 mole). The mixture was stirred at room temperature for 10 minutes and lactobiono-1,5-lactone (10.9 g, 0.03 mole) added followed by heating at reflux for 1 hour. Activated charcoal was then added and the reaction mixture stirred for 15 minutes at reflux. Activated charcoal was removed by filtration over a bed of celite while warm, washed with methanol (3×50 ml) and the filtrate allowed to cool to room temperature. The solvent was removed by rotary evaporation, the product washed with ethyl ether (2×100 ml), filtered and dried in a vacuum oven at room temperature over phosphorous pentoxide giving 14.0 g (75% yield) of N-D-lactobionyl dodecyl glycinate.

Example 68

(1 Ester Heteroatom)

Preparation of N-D-Lactobionyl Dodecyl β-Alaninate

A 25 ml round bottom flask equipped with a condenser, thermometer and stir bar was charged with dodecyl β-alaninate hydrochloride (3.0 g, 0.01 mole) and 2.0M methanolic ammonia (5 ml, 0.01 mole). The mixture was stirred at room temperature for 10 minutes and lactobiono-1,5-lactone (3.5 g, 0.01 mole) added followed by heating at reflux for 1 hour. Activated charcoal was then added and the reaction mixture stirred for 15 minutes at reflux. Activated charcoal was removed by filtration over a bed of celite while warm, washed with methanol (3×25 ml) and the filtrate allowed to cool to room temperature. The solvent was removed by rotary evaporation, the product washed with ethyl ether (2×50 ml), filtered and dried in a vacuum oven at room temperature over phosphorous pentoxide giving 4.3 g (70% yield) of N-D-lactobionyl dodecyl β-alaninate.

Example 69

(1 Amino Heteroatom)

Preparation of Cocoaminopropyl D-Lactobionamide

A 2 liter round bottom flask equipped with a condenser, addition funnel, thermometer and mechanical stirrer was charged with D-lactobion-1,5-lactone (66.4 g, 0.20 mole), methanol (175 g for 40% total solids) and methanesulfonic acid (3 drops). The suspension was heated to 50° C. over 15 minutes and the heating mantle removed. Cocoaminopropylamine (50.0 g, 0.20 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 96.9 g (83% yield) of cocoaminopropyl D-lactobionamide with a melting point of 97°–101° C.

Example 70

(1 Amino Heteroatom)

Preparation of Oleylaminopropyl D-Lactobionamide

A 2 liter round bottom flask equipped with a condenser, addition funnel, thermometer and mechanical stirrer was charged with D-lactobion-1,5-lactone (52.7 g, 0.15 mole), methanol (103 g for 50% total solids) and methanesulfonic acid (4 drops). The suspension was heated to 50° C. over 15 minutes and the heating mantle removed. Oleylaminopropylamine (50.0 g, 0.15 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 93.1 g (91% yield) of oleylaminopropyl D-lactobionamide with a melting point of 117°–118° C.

Example 71

(1 Amino Heteroatom)

Preparation of Hydrogenated Tallowaminopropyl D-Lactobionamide

A 1 liter round bottom flask equipped with a condenser, addition funnel, thermometer and mechanical stirrer was charged with D-lactobiono-1,5-lactone (20.0 g, 0.06 mole) and methanol (50 g). The suspension was heated to 40° C. over 15 minutes and the heating mantle removed. Hydrogenated tallowaminopropylamine (19.0 g, 0.06 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (84% yield) of hydrogenated tallowaminopropyl D-lactobionamide with a melting point of 135°–137° C.

Example 72

(1 Amino and 1 Ether Heteroatom)

Preparation of Dodecyl to Pentadecyloxyprolaminopropyl D-Lactobionamide

A 2 liter round bottom flask equipped with a condenser, addition funnel, thermometer and mechanical stirrer was charged with D-lactobion-1,5-lactone (53.6 g, 0.16 mole), methanol (104 g for 50% total solids) and methanesulfonic acid (3 drops). The suspension was heated to 50° C. over 15 minutes and the heating mantle removed. Dodecyl to pentadecyloxypropylaminopropylamine (50.0 g, 0.16 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 91.3 g (88% yield) of dodecyl to pentadecyloxypropylaminopropyl D-lactobionamide with a melting point of 107°–111° C.

Example 73

(5 Ether Heteroatoms)

Preparation of Dodecyloxypropyl D-Maltobionamide Tetraoxethylene ether

A 100 g autoclave equipped with a pressure gauge, mechanical stirrer, rupture disk, gas inlet and gas outlet was charged with dodecyloxypropyl D-maltobionamide (4.5 g, 7.49×10-3 mole) dissolved in tert-butanol (20 g) and triethylamine (0.45 g, 4.45×10$^{-3}$ mole). The autoclave was flushed with a blanket of nitrogen and a mild vacuum pulled. Ethylene oxide (1.3 g, 3.0×10$^{-2}$ mole) was then added and the mixture heated to 70° C.–80° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 1N hydrochloric acid followed by removal of tert-butanol by vacuum distillation giving 6.4 g of dodecyloxypropyl D-maltobionamide tetraoxyethylene ether.

Example 74

(1 Amide and 1 Ether Heteroatom)

Preparation of Dodecyl to Pentadecyloxypropylpropionamidopropyl D-Lactobionamide in Solvent A 50 ml round bottom flask equipped with a condenser, addition funnel, thermometer and mechanical stirrer was charged with dodecyl to pentadecyloxypropylaminopropyl D-lactobionamide (3.0 g, 4.40×10$^{-3}$ mole) and methanol (20 g). The suspension was heated to 35° C. and propionic anhydride (1.7 g, 1.32×10$^{-2}$ mole) was added dropwise over 15 minutes with rapid stirring. The reaction mixture was heated at room temperature for 24 hours and the solvent, propionic acid and excess anhydride was removed by vacuum distillation (3.1 g, 95% yield).

Example 75

(No Heteroatom)

Preparation of Dodecyl(Methyl β-D-Glucofuranosid)uronamide (I) D-Glucurono-6,3-lactone (100.0 g, 0.57 mole), anhydrous methanol (200.0 g, 6.24 moles), and methanesulfonic acid (3 drops) were placed in an oven dried three-necked round bottom flask equipped with mechanical stirrer, thermometer and condenser. The mixture was heated for 24 hours at reflux, cooled and neutralized with 0.1N methanolic KOH. The mixture was filtered and washed with cold methanol (20 ml) yielding 20.9 g of methyl b-D-glucofuranosidurono-6,3-lactone (MbGlucl). By further concentration of the filtrate an additional 28.2 g of MbGlucl was isolated giving a total yield of 49.1 g (45.3%), MP=139° C., purity=99.1% (GC).

(II) Methyl b-D-glucofuranosidurono-6,3-lactone (20.0 g, 0.11 mole), anhydrous methanol (20 ml), and anhydrous acetonitrile (50 ml) were placed in a three-necked round bottom flask equipped with a mechanical stirrer, thermometer and condenser. The mixture was heated to 40° C. and N-dodecylamine (19.5 g, 0.11 mole) dissolved in anhydrous acetonitrile (10 ml) added dropwise. The solution was allowed to stand overnight at room temperature, filtered, and washed with acetonitrile (2×25 ml) giving a yield of 24.7 g (77.3%), MP=90°–91° C., purity=99.3% (GC).

Example 76

(No Heteroatom)

Preparation of Tetradecyl(Methyl β-D-Glucofuranosid)uronamide

Prepared as in Example 73 except N-tetradecylamine (23.5 g, 0.11 mole) was used. The yield was 37.8 g (87.0%), purity=98.5% (GC).

Example 77

(No Heteroatom)

Preparation of Dodecyl(Methyl D-Glucosid) uronamide (I) D-Glucurono-6,3-lactone (25.0 g, 0.14 mole), anhydrous methanol (225 ml, 5.55 moles) and p-toluenesulfonic acid (2.14 g, 0.011 mole) were placed in a three-necked round bottom flask equipped with a mechanical stirrer, thermometer and condensor. The mixture was heated for 24 hours at reflux, cooled and neutralized with methanolic KOH. A sample was taken and analyzed and found to contain a mixture of methyl β-D-glucofuranosidurono-6,3-lactone, methyl(methyl a-D-glucopyranosid)uronate and methyl(methyl β-D-glucopyranosid)uronate.

(II) Dodecylamine (26.0 g, 0.14 mole) was added to an anomeric mixture of methyl(methyl D-glucosid)uronate in methanol and heated to 55° C. for eight hours. Methanol was removed (125 ml) giving a yield of 51.1 g (97.0%).

Example 78

(No Heteroatom)

Preparation of Decyl(Methyl α-D-Galactopyranosid)uronamide (I) D-Galacturonic acid monohydrate (97%, 25.0 g, 0.12 mole) and 0.1N methanolic HCl (300 ml, 7.41 moles) were placed in a three-necked round bottom flask equipped with a mechanical stirrer, thermometer, and condenser. The mixture was heated for 24 hours at reflux, cooled and neutralized with 1N methanolic KOH. Excess methanol was removed and ethanol (75 ml) added. The solution was cooled to 0° C., potassium chloride filtered and washed with cold ethanol (20 ml). The filtrate was concentrated to about 40 ml, heated to 40° C. and enough ether added to make the solution turbid. After standing at room temperature overnight, 6.5 g of methyl(methyl α-D-galactopyranosid)uronate was isolated and washed with cold ethanol/ether solution (20 ml). By further concentration of the filtrate, an additional 1.0 g of product was isolated, giving a total yield of 7.5 g (28.7%), MP=139°–140° C., purity=98.2% (GC).

(II) Methyl(methyl a-D-galactopyranosid)uronate (2.0 g, 0.009 mole), anhydrous methanol (15 ml) and N-decylamine (4.25 g, 0.027 mole) were placed in a three-necked round bottom flask equipped with a mechanical stirrer, thermometer and short path distillation head. The mixture was heated for ½ hour at reflux. The methanol was removed, heptane (35 ml) added and stirred rapidly. The product was filtered, washed with heptane (3×20 ml) and dried giving 2.3 g (73.6%). One recrystallization from aqueous ethanol yielded 1.8 g (57.5%) of pure product, MP=180°–181° C., purity=99.3% (GC).

Example 79

(1 Ether Heteroatom)

Preparation of Octyl/decyloxypropyl (Methyl D-Glucosid)uronamide

Octyl/decylamine (21.6 g, 0.10 mole) was added to an anomeric mixture of methyl(methyl D-glucosid)uronate (22.4 g, 0.10 mole) in methanol and heated to 55° C. for eight hours. Methanol was removed (125 ml) giving a yield of 38.8 g (95.1%).

Example 80

(No Heteroatom)

Preparation of Sodium Heptyl D-Gluconamide Monosulfate (Comparative)

A 2000 ml four necked round bottom flask equipped with a condenser, addition funnel, thermometer and mechanical stirrer was charged with heptyl D-gluconamide (60.4 g, 0.21 mole) and methylene chloride (754.2 g). Under a mild nitrogen sparge, chlorosulfonic acid (24.0 g, 0.21 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give a yield of 89.6%.

Example 81

(No Heteroatom)

Preparation of Sodium Heptyl D-Gluconamide Disulfate (Comparative)

A 2000 ml four necked round bottom flask equipped with a condenser, addition funnel, thermometer and mechanical stirrer was charged with heptyl D-gluconamide (50.0 g, 0.17 mole) and methylene chloride (805.5 g). Under a mild nitrogen sparge, chlorosulfonic acid (39.6 g, 0.34 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give a yield of 80.8%.

Example 82

(No Heteroatom)

Preparation of Sodium Dodecyl D-Gluconamide Monosulfate (Comparative)

A 500 ml four necked round bottom flask equipped with a condenser, addition funnel, thermometer and mechanical stirrer was charged with dodecyl D-gluconamide (10.0 g, $2.75 \times 10^{-2}$ mole) and methylene chloride (200 ml). Under a mild nitrogen sparge, chlorosulfonic acid (3.2 g, 2.75×10$^{-2}$ mole) was added dropwise over 1 hour with rapid agitation. Increase the nitrogen sparge rate and stir at room temperature for several hours. Remove methylene chloride under a mild house vacuum, add water (100 ml) and neutralize the product to a pH about 7 with 10% sodium hydroxide. The water was removed by freeze drying to give a yield of 97.5%.

Example 83

(No Heteroatom)

Preparation of Sodium Dodecyl D-Gluconamide Sesquisulfate (Comparative)

A 3000 ml four necked round bottom flask equipped with a condenser, addition funnel, thermometer and mechanical stirrer was charged with dodecyl D-gluconamide (242.3 g, 0.67 mole) and methylene chloride (1500 ml). Under a mild nitrogen sparge, the reaction mixture was heated to reflux. Add chlorosulfonic acid (116.5 g, 1.00 mole) dropwise over 1 hour with rapid agitation. Increase the nitrogen sparge rate and stir at room temperature for several hours. Remove methylene chloride under a mild house vacuum, add 50% aqueous ethanol (1200 ml) and neutralize the product with 10% sodium hydroxide. The ethanol was removed under vacuum and water removed by freeze drying to give a yield of 93.4%.

Example 84

(No Heteroatom)

Preparation of Sodium Coconut D-Gluconamide Sesquisulfate (Comparative)

A 3000 ml four necked round bottom flask equipped with a condenser, addition funnel, thermometer and mechanical stirrer was charged with coconut D-gluconamide (249.6 g, 0.67 mole) and methylene chloride (1300 ml). Under a mild nitrogen sparge, heat the reaction mixture under reflux. Add chlorosulfonic acid (116.5 g, 1.00 mole) dropwise over 1 hour with rapid agitation. Increase the nitrogen sparge rate and stir at room temperature for several hours. Remove methylene chloride under a mild house vacuum, add 50% aqueous ethanol (1200 ml) and neutralize the product with 10% sodium hydroxide. The ethanol was removed under vacuum and water removed by freeze drying to give a yield of 87.0%.

Example 85

(No Heteroatom)

Preparation of Sodium Tallow D-Gluconamide Disulfate (Comparative)

A 2000 ml four necked round bottom flask equipped with a condenser, addition funnel, thermometer and mechanical stirrer was charged with tallow D-gluconamide (100.0 g, 0.23 mole) and methylene chloride (1380 g). Under a mild nitrogen sparge, chlorosulfonic acid (52.6 g, 0.46 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give yield of 95.9%.

Example 86

(No Heteroatom)

Preparation of Sodium Oleyl D-Gluconamide Disulfate (Comparative)

A 2000 ml four necked round bottom flask equipped with a condenser, addition funnel, thermometer and mechanical stirrer was charged with oleyl D-gluconamide (100.0 g, 0.22 mole) and methylene chloride (1371 g). Under a mild nitrogen sparge, chlorosulfonic acid (51.3 g, 0.44 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give a yield of 98.3%.

Example 87

(No Heteroatom)

Preparation of Sodium Oleyl D-Gluconamide Disulfate in the Presence of a Color Improvement Agent (The Invention)

A 2000 ml four necked round bottom flask equipped with a condenser, addition funnel, thermometer and mechanical stirrer was charged with oleyl D-gluconamide (100.0 g, 0.22 mole) and methylene chloride (1371 g). Under a mild nitrogen sparge, chlorosulfonic acid (51.3 g, 0.44 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. Add 3% hydrogen peroxide (2 ml) and let stir overnight at room temperature. The ethanol was removed under vacuum and water removed by freeze drying to give a yield of 97.4%.

Example 88

(No Heteroatom)

Preparation of Sodium Coco D-Gluconamide Sequisulfate in the Presence of a Color Improvement Agent (The Invention)

A 2000 ml four necked round bottom flask equipped with a condenser, addition funnel, thermometer and mechanical stirrer was charged with coco D-gluconamide (50.0 g, 0.13 mole) and methylene chloride (650 g). Under a mild nitrogen sparge, chlorosulfonic acid (22.8 g, 0.20 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. Add 3% hydrogen peroxide (1 ml) and let stir overnight at room temperature. The ethanol was removed under vacuum and water removed by freeze drying to give a yield of 94.8%.

Example 89

(1 Ether Heteroatom)

Preparation of Sodium C8/C10 oxypropyl D-Gluconamide Monosulfate in the Presence of a Color Improvement Agent (The Invention)

A 2000 ml four necked round bottom flask equipped with a condenser, addition funnel, thermometer and mechanical stirrer was charged with C8/C10 oxypropyl D-gluconamide (60.0 g, 0.15 mole) and methylene chloride (800 g). Under a mild nitrogen sparge, chlorosulfonic acid (17.3 g, 0.15 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. Add 3% hydrogen peroxide (1 ml) and let stir overnight at room temperature. The ethanol was removed under vacuum and water removed by freeze drying to give a yield of 95.9%.

Example 90

(1 Ether Heteroatom)

Preparation of Sodium Dodecyloxypropyl D-Gluconamide Monosulfate (The Invention)

A 500 ml four necked round bottom flask equipped with a condenser, addition funnel, thermometer and mechanical stirrer was charged with dodecyloxypropyl D-gluconamide (21.4 g, 0.05 mole) and methylene chloride (230 g). Under a mild nitrogen sparge, chlorosulfonic acid (5.9 g, 0.05 mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give yield of 95.9%.

Example 91

(No Heteroatom)

Preparation of Sodium Tetradecyl (Methyl β-D-Glucofuranosid)uronamide Disulfate (The Invention)

A four necked round bottom flask equipped with a condenser, addition funnel, thermometer and mechanical stirrer was charged with tetradecyl(methyl β-D-glucofuranosid)uronamide (5.0 g, $1.24 \times 10^{-2}$ mole) and methylene chloride (71 g). Under a mild nitrogen sparge, chlorosulfonic acid (2.9 g, $2.48 \times 10^{-2}$ mole) was added dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give a yield of 98.6%.

Example 92

(1 Ether Heteroatom)

Preparation of Sodium C8/C10 oxypropyl(Methyl D-Glucofuranosid)uronamide Monosulfate (The Invention)

A four necked round bottom flask equipped with a condenser, addition funnel, thermometer and mechanical stirrer was charged with C8/C10 oxypropyl(methyl D-glucofuranosid)uronamide (10.00 g, $2.46 \times 10^{-2}$ mole) and methylene chloride (70 g). Under a mild nitrogen sparge, heat the reaction mixture to reflux. Add chlorosulfonic acid (2.87 g, $2.46 \times 10^{-2}$ mole) dropwise over 1 hour with rapid agitation. Increase the nitrogen sparge rate and stir at room temperature for several hours. Remove methylene chloride under a mild house vacuum, add 50% aqueous ethanol and neutralize the product with 10% sodium hydroxide. The ethanol was removed under vacuum and water removed by freeze drying to give a yield of 93.9%.

Example 93

(No Heteroatom)

Preparation of Potassium Coco D-Lactobionamide Sesquisulfate (The Invention)

A 500 ml four necked round bottom flask equipped with a condenser, addition funnel, thermometer and mechanical stirrer was charged with coconut lactobionamide (10 g, 1 eq) and chloroform (250 ml). Under a mild nitrogen sparge, chlorosulfonic acid (3.2 g, 1.5 eq) was added dropwise over 1 hour with rapid agitation. Increase the nitrogen sparge rate and stir at room temperature for several hours. Methanolic potassium hydroxide (1.54 g/50 ml) was added dropwise. Removal of chloroform/methanol gave nearly quantitative yield of potassium coco lactobionamide sesquisulfate.

Example 94

(No Heteroatom)

Preparation of Potassium Tallow D-Lactobionamide Sesquisulfate (The Invention)

A 500 ml four necked round bottom flask equipped with a condenser, addition funnel, thermometer and mechanical stirrer was charged with tallow lactobionamide (10 g, 1 eq) and chloroform (350 ml). Under a mild nitrogen sparge, chlorosulfonic acid (2.9 g, 1.5 eq) was added dropwise over 1 hour with rapid agitation. Increase the nitrogen sparge rate and stir at room temperature for several hours. Methanolic potassium hydroxide (1.54 g/50 ml) was added dropwise. Removal of chloroform/methanol gave nearly quantitative yield of potassium tallow lactobionamide sesquisulfate.

Example 95

(No Heteroatom)

Preparation of Sodium Tetradecyl D-Lactobionamide Sesquisulfate (The Invention)

A 1000 ml four necked round bottom flask equipped with a condenser, addition funnel, thermometer and mechanical stirrer was charged with tetradecyl lactobionamide (20 g, 1 eq) and chloroform (450 ml). Under a mild nitrogen sparge, chlorosulfonic acid (4.4 g, 1.5 eq) was added dropwise over 1 hour with rapid agitation. Increase the nitrogen sparge rate and stir at room temperature for several hours. Methanolic sodium hydroxide (2.16 g/100 ml) was added dropwise. Removal of chloroform/methanol gave nearly quantitative yield of sodium tetradecyl lactobionamide sesquisulfate.

Example 96

(No Heteroatom)

Preparation of Sodium Hexadecyl D-Lactobionamide Sesquisulfate (The Invention)

A 1000 ml four necked round bottom flask equipped with a condenser, addition funnel, thermometer and mechanical stirrer was charged with hexadecyl lactobionamide (20 g, 1 eq) and chloroform (450 ml). Under a mild nitrogen sparge, chlorosulfonic acid (5.9 g, 1.5 eq) was added dropwise over 1 hour with rapid agitation. Increase the nitrogen sparge rate and stir at room temperature for several hours. Methanolic sodium hydroxide (2.05 g/100 ml) was added dropwise. Removal of chloroform/methanol gave nearly quantitative yield of sodium hexadecyl lactobionamide sesquisulfate.

Example 97

(No Heteroatom)

Preparation of Sodium Hexadecyl D-Lactobionamide(2.5)Sulfate (The Invention)

A 1000 ml four necked round bottom flask equipped with a condenser, addition funnel, thermometer and mechanical stirrer was charged with hexadecyl lactobionamide (20 g, 1 eq) and chloroform (450 ml). Under a mild nitrogen sparge, chlorosulfonic acid (9.9 g, 2.5 eq) was added dropwise over 1 hour with rapid agitation. Increase the nitrogen sparge rate and stir at room temperature for several hours. Methanolic sodium hydroxide (3.4 g/150 ml) was added dropwise. Removal of chloroform/methanol gave quantitative nearly yield of sodium hexadecyl lactobionamide(2.5)sulfate Examples 98–101

Surface-Activity (Surfactancy) of Anionic Sugar Based Surfactants

In order to demonstrate the effectiveness of the anionic sugar based surfactants of the invention as surface active agents, various physical properties such as Krafft point, clarity improvement, foam height and zein dissolution were measured. In particular, the properties of these new anionic surfactants compared well to some commonly known petrochemically based anionic surfactants such as sodium dodecyl sulfate (SDS) and sodium dodecanoyl isethionate (SDI). The results are set forth in Examples 98 to 101 below.

Example 98

Krafft Point

The temperature at which a surfactant begins to form micelles instead of a precipitate is referred to as the Krafft point. At this temperature the solubility of a surfactant becomes equal to its critical micelle concentration (CMC). In general, surfactants with low Krafft point values are preferred, since these materials offer the advantage of enhanced water solubility and detergency at cold temperatures. The Krafft point was measured by preparing a 1.0% dispersion of anionic surfactant in water by weight. If the surfactant was soluble at room temperature, the solution was slowly cooled to 0° C. If the surfactant did not precipitate out of solution, the Krafft point was considered to be 0° C. If precipitation occurs during cooling, the temperature at which precipitation occurs was taken as the Krafft point. If the surfactant was insoluble at room temperature, the dispersion was slowly heated until the solution became homogeneous. At that temperature the Krafft point was taken. The Krafft point of various surfactants are set forth below:

The Krafft Point of Various Surfactants in Water

| The Krafft Point of Various Surfactants in Water | |
|---|---|
| Surfactant | Krafft Point (°C.) |
| Potassium Coco D-Lactobionamide Sesquisulfate | 0 |
| Coco D-Lactobionamide (Comparative) | <6 |
| Potassium Tetradecyl D-Lactobionamide Sesquisulfate | 0 |
| Tetradecyl D-Lactobionamide (Comparative) | 46 |
| Potassium Tallow D-Lactobionamide Sesquisulfate | 0 |
| Tallow D-Lactobionamide (Comparative) | >46 |
| Sodium C8/C10 Oxypropyl D-Gluconamide Monosulfate | 0 |
| C8/C10 Oxypropyl D-Gluconamide (Comparative) | 48 |
| Dodecyl D-Gluconamide (Comparative) | Insoluble |
| Sodium Tetradecyl(Methyl β-D-Glucofuranosid)uronamide Disulfate | 0 |
| Tetradecyl(Methyl β-D-Glucofuranosid)uronamide (Comparative) | Insoluble |
| Sodium Dodecyl Sulfate (Comparative) | 14 |
| Sodium Dodecanoyl Isethionate (Comparative) | 24 |

From the above table it can be seen that the anionic sugar based surfactants of the present invention have significantly lower Krafft points (°C.) than all comparatives. This finding suggests that the anionic sugar based surfactants of the present invention are ready soluble in water at low temperature which make them especially suitable for low temperature washing and cleansing applications. This finding has not been disclosed in the art.

Example 99

Clarity Improvement

An essential condition for a composition to be successful is its appearance. Compositions that become turbid or produce sedimentation upon storage or standing in water are seen by the consumer as being inferior. Non-sulfated alkyl aldonamides and alkyl(glycosid)uronamides are examples of materials that are difficult to formulate and are generally unstable in formulations at high concentrations. Therefore an simple test has been devised to determine its easy of formulation. The test (clarity test) involves dissolving the surfactant in water and noting its appearance. The clarity of various surfactants are set forth below:

The Clarity of Various Surfactants in Water at
Room Temperature

| Surfactant | Appearance | ANC |
|---|---|---|
| Potassium Tetradecyl D-Lactobionamide Sesquisulfate | Clear | 14.0 |
| Tetradecyl D-Lactobionamide (Comparative) | Cloudy | 14.0 |
| Potassium Tallow D-Lactobionamide Sesquisulfate | Clear | 17.2 |
| Tallow D-Lactobionamide (Comparative) | Cloudy | 17.2 |
| C8/C10 Oxypropyl D-Gluconamide Monosulfate | Clear | 11.6 |
| Sodium Dodecyl D-Gluconamide Monosulfate (Comparative) | Hazey | 12.0 |
| Sodium Dodecyl D-Gluconamide Sesquisulfate (Comparative) | Hazey | 12.0 |
| Sodium Dodecyl D-Gluconamide Disulfate (Comparative) | Clear | 12.0 |
| Dodecyl D-Gluconamide (Comparative) | Ins ppt | 12.0 |
| Sodium Tetradecyl(Methyl β-D-Glucofuranosid)uronamide Disulfate | Clear | 14.0 |
| Tetradecyl(Methyl β-D-Glucofuranosid)uronamide (Comparative) | Ins ppt | 14.0 |

ANC = Average Number of Carbons in the Alkyl Chain
Ins ppt = Insoluble Precipitate From the above table it can be seen that, the anionic sugar based surfactants of the invention provide enhanced water solubility and improved clarity in water, particularly at room temperature (21° C.). This finding suggests that aqueous compositions comprising anionic sugar based surfactants of the invention should not become turbid or produce sedimentation upon storage or standing in water. This materials are therefore generally easier to formulate and can be present in formulations at much higher concentrations.

Example 100

Foam Height

The generation of a thick stable foam is important, because consumers are accustomed to, and expect compositions, (particulary dishwashing detergent compositions), to produce a copious rich foam. Compositions that do not generate sufficient foam are often seen as inferior. Most of the foaming data on surfactants are typically obtained by the Ross-Miles method (ASTM D1173–53; Oil & Soap 62:1260, 1958). In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette (initial foam height) and then again after a given amount of time. Using this method, the foam production (initial foam height) and foam stability (final foam height after 10 minutes) of the anionic sugar based surfactants of the invention were measured at 0.1% surfactant concentration 40° C. and 0 ppm (parts per million) hardness. The foam height of various surfactants are set forth below:

The Foam Height of Various Surfactants in Water

| Surfactant | Foam Height (mm) | |
|---|---|---|
| | IFH | FFH |
| Potassium Coco D-Lactobionamide Sesquisulfate | 152 | 144 |
| Potassium Coco D-Lactobionamide (2.5) Sulfate | 150 | 143 |
| Potassium Coco D-Lactobionamide (2.5) Sulfate/Coco D-Lactobionamide | 160 | 155 |
| Coco D-Lactobionamide (Comparative) | 155 | 143 |
| Potassium Tetradecyl D-Lactobionamide Sesquisulfate | 168 | 163 |
| Tetradecyl D-Lactobionamide (Comparative) | 150 | 143 |
| Potassium Tallow D-Lactobionamide Sesquisulfate | 156 | 152 |
| Tallow D-Lactobionamide (Comparative)[a] | 99 | 94 |
| Sodium C8/C10 Oxypropyl D-Gluconamide Monosulfate | 158 | 150 |
| Sodium Dodecyl D-Gluconamide Monosulfate (Comparative) | 145 | 139 |
| Dodecyl D-Gluconamide (Comparative) | Insoluble | |
| Sodium Dodecyl Sulfate (Comparative) | 160 | 150 |

IFH = Initial Foam Height, FFH = Final Foam Height
a — Foam Height Measured at 50° C.

From the above table it can be seen that the anionic sugar based surfactants of the present invention generally provide improved foam (similar to sodium dodecyl sulfate). Closer observation of the table reveals that potassium coco D-lactobionamide(2.5)sulfate tends to foam as well as its comparative, coco D-lactobionamide. The foam height of this compound can be improved by adding coco D-lactobionamide in ratios of about 50% by weight or less. This is an example where complete sulfation is not required and partial sulfation is more favorable. The mixture of potassium coco D-lactobionamide(2.5)sulfate and coco lactobionamide (50:50) has better foam profile than either one alone.

Example 101

Zein Solubilization Assay (Mildness Potential)

Many factors have been reported to have an influence on skin irritation such as removal of skin lipids, loss of naturally occurring hygroscopic materials in the stratum corneum, adsorption, protein denaturation, and epidermal lyposomal injury. Although there are many hypotheses regarding skin irritation, it is generally believed that surfactants become irritants because they penetrate the stratum corneum and then react with the inner cells of the epidermis. Traditionally, the study of percutaneous absorption has focused on measuring the diffusion of chemicals through the stratum corneum. Diffusion through an organ as complex as skin and its associated adnexal appendages is challenging to measure and model. Another challenge of cutaneous metabolism is to asses the irritating potential, toxicity, and therapeutic potential of the penetrating compounds. It has been shown that in vitro mildness tests tend to correlate well within vivo tests. For example, Gotte, in Proc. Int. Cong. Surface Active Subs., 4th Brussels (1964), 3, 83–90 and Schwinger in Kolloid-Z.Z.Poly., (1969), 233 898 have shown that a surfactant's ability to solubilize zein, an insoluble maize protein, correlates well with surfactant irritation potential. More specifically, the greater the zein solubilization, the greater the irritation potential of a surfactant. In order to test irritancy potential, a 1% solution of surfactant (30 mls) was added to 1.5 g zein and stirred at room temperature for one hour. Residual zein was collected and dried to constant weight. Differences between starting and residual weights were used to calculate % zein solubilized.

The Zein Number of Various Surfactants in Water at Room Temperature

| Surfactant | % Zein Solubilized |
| --- | --- |
| Sulfated Polyhydroxy Anionic Surfactants | ~18–35 |
| Sodium Dodecyl Sulfate (Comparative) | 86 |
| Sodium Isethionate (Comparative) | 55 |
| No Surfactant (Control) | 9 |

From the above table it can be seen that the anionic sugar based surfactants of the present invention dissolve little zein and are therefore potentially mild to the skin. These compounds are believed to be more mild than sodium dodecyl sulfate and sodium dodecanoyl isethionate, two typical petrochemically anionic surfactants.

Example 102

Color Improvement

The anionic sugar based surfactants of the invention are generally isolated as off white to pale yellow crystalline solids. It has been found in accordance to the present invention, that use of color improvement agents such as bleaching or reducing agents, can consistently provide anionic sugar based surfactants having superior color. Compounds treated in this manner produce products that are isolated as stable white crystalline solids which form clear water white solutions (as well as water white compositions). It has also been shown that treated (T) anionic sugar based surfactants of the invention remain of good color at room temperature for more than 24 months. The color improvement of various surfactants are set forth below:

The Color Improvement of Various Surfactants (24 Months)

| Surfactant | Color (Solid) | Color in Water |
| --- | --- | --- |
| Sodium C8/C10 Oxypropyl D-Gluconamide Monosulfate (T) | w | wws |
| Sodium Coco D-Gluconamide Sequisulfate (T) | w | wws |
| Sodium Coco D-Gluconamide Sequisulfate (Comparative) | y | ys |
| Sodium Oleyl D-Gluconamide Disulfate (T) | w | wws |
| Sodium Oleyl D-Gluconamide Disulfate (Comparative) | y | ys |

(T) = Treated with a Color Improvement Agent
w = White Crystalline Solid
wws = Clear Water White Solution
y = Off White to Pale Yellow Crystalline Solid
ys = Pale Yellow Solution From the above table it can be seen that the anionic sugar based surfactants of the invention, which are treated with a color improvement agent (Examples 87 to 89), produce stable white crystalline solids and dissolve in water to form colorless water white solutions.

It should be understood that the specific forms of the invention herein which are illustrated and described, are intended to be representative only. Changes, including but not limited to those suggested in this specification, may be made in the illustrated embodiments without departing from the clear teachings of the disclosure. For instance, any of the substrates in Examples (1 through 79) can be sulfated according to the methods of the invention to provide additional anionic sugar based surfactants. Accordingly, reference should be made to the following appended claims in determining the full scope of the invention.

What is claimed is:

1. A sulfated alkyl aldobionamide compound having the formula:

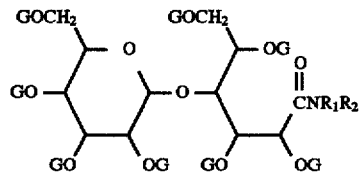

wherein:

G is a mixture of hydrogen (H) and at least one $SO_3X$ group, or a mixture of hydrogen (H), a polyoxyethylene, polyoxypropylene group and at least one $SO_3X$ group;

$R_1$ is hydrogen (H), a $C_1$–$C_{18}$ straight or branched chain, saturated or unsaturated hydrocarbon group;

$R_2$ is a $C_1$–$C_{26}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$, wherein $R_1$ is defined as $R_1$ above), sulfur (S), sulfur monoxide (SO), sulfur dioxide ($SO_2$), sulfamate ($NSO_3X$), hydroxy (CHOH or $C(OH)_2$); and X is hydrogen (H), an alkali metal, alkaline earth metal, ammonium group, alkyl ammonium group, mono-, di-, or trialkanol ammonium group, basic amino acid or mixtures thereof.

2. An alkyl aldobionamide compound according to claim 1, wherein $R_1$ is hydrogen, a $C_1$ to $C_8$ hydrocarbon, 2-hydroxyethyl, 2-hydroxypropyl; and $R_2$ is a $C_6$–$C_{24}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$), hydroxy (CHOH or $C[OH]_2$); and X is hydrogen (H), an alkali metal, alkaline earth metal, ammonium group, alkyl ammonium group, mono-, di-, or trialkanol ammonium group, basic amino acid or mixtures thereof.

3. An alkyl aldobionamide according to claim 2, wherein:

G is a mixture of hydrogen (H) and at least one $SO_3X$ group;

$R_1$ is hydrogen (H), a $C_1$–$C_6$ hydrocarbon, 2-hydroxyethyl, 2-hydroxypropyl group;

$R_2$ is a $C_8$–$C_{22}$ straight or branched chain, saturated or unsaturated hydrocarbon group that may be interrupted with at least one heteroatom selected from the group consisting of ether (O), amide ($NR_1CO$, $CONR_1$ or $NCOR_1$), hydroxy (CHOH or $C(OH)_2$); and X is hydrogen (H), an alkali metal, alkaline earth metal, ammonium group, alkyl ammonium group, mono-, di-, or trialkanol ammonium group, basic amino acid or mixtures thereof.

4. A sulfated alkyl aldobionamide composition comprised of a mixture of the compounds of claim 1 having the formula:

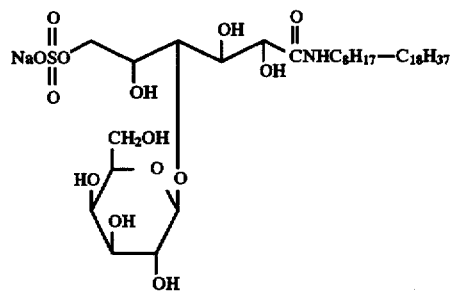

wherein:

G is a mixture of hydrogen (H) and one $SO_3X$ group;

$R_1$ is hydrogen (H);

$R_2$ is $C_8H_{17}$ (5%), $C_{10}H_{21}$ (7%), $C_{12}H_{25}$ (50%), $C_{14}H_{29}$ (18%), $C_{16}H_{33}$ (10%), $C_{18}H_{37}$ (6%), $C_{18}H_{35}$ (4%);

and X is sodium (Na).

5. A sulfated alkyl aldonamide composition comprised of a mixture of the compounds of claim 1 having the formula:

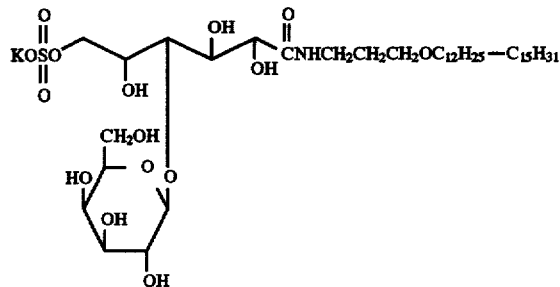

wherein:

G is a mixture of hydrogen (H) and one $SO_3X$ group;

$R_1$ is hydrogen (H);

$R_2$ is $(CH_2)_3OC_{12}H_{25}$ (25%), $(CH_2)_3OC_{13}H_{27}$ (39%), $(CH_2)_3OC_{14}H_{29}$ (21%), $(CH_2)_3OC_{15}H_{31}$ (15%); and X is potassium (K).

6. A sulfated alkyl aldobionamide composition comprised of a mixture of the compounds of claim 1 having the formula:

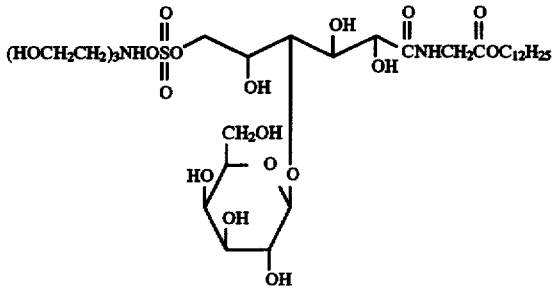

wherein:

G is a mixture of hydrogen (H) and one $SO_3X$ group;

$R_1$ is hydrogen (H);

$R_2$ is $CH_2COOC_{12}H_{25}$;

and X is triethanolamine (($HOCH_2CH_2)_3NH$).

7. A disulfated alkyl aldobionamide composition comprised of a mixture of the compounds of claim 1 having the formula:

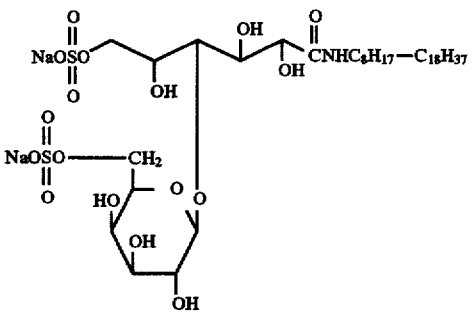

wherein:

G is a mixture of hydrogen (H) and two $SO_3X$ groups;

$R_1$ is hydrogen (H);

$R_2$ is $C_8H_{17}$ (5%), $C_{10}H_{21}$ (7%), $C_{12}H_{25}$ (50%), $C_{14}H_{29}$ (18%), $C_{16}H_{33}$ (10%), $C_{18}H_{37}$ (6%), $C_{18}H_{35}$ (4%);

and X is sodium (Na).

8. A sulfated heteroatom containing aldonamide having the formula:

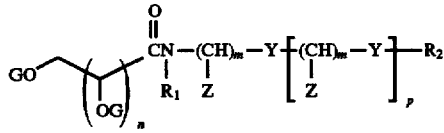

wherein:

G is a mixture of hydrogen (H) and at least one $SO_3X$ group, or a mixture of hydrogen (H), polyoxyethylene, polyoxypropylene and at least one $SO_3X$ group;

$R_1$ is hydrogen (H), a $C_1$–$C_{18}$ straight or branched chain, saturated or unsaturated hydrocarbon group or mixtures thereof;

$R_2$ is a $C_1$–$C_{26}$ straight or branched chain, saturated or unsaturated hydrocarbon group or mixtures thereof;

X is hydrogen (H), an alkali metal, alkaline earth metal, ammonium group, alkyl ammonium group, mono-, di-, or trialkanol ammonium group, basic amino acid or mixtures thereof;

Y=amine (NH), ether (O), ester (COO or OOC), amide (NR$_1$CO, CONR$_1$ or NCOR$_1$, wherein R$_1$ is defined as R$_1$ above), sulfur (S), sulfur monoxide (SO), sulfur dioxide (SO$_2$), sulfamate (NSO$_3$X), hydroxy (CHOH or C(OH)$_2$) group or mixtures thereof;

n=1–8;

m=1–8;

p=0–35; and

Z=hydrogen (H) or hydrogen and at least one methyl group.

9. A sulfated heteroatom containing aldonamide according to claim 8, wherein:

R$_1$ is hydrogen (H), a C$_1$–C$_8$ hydrocarbon, 2-hydroxyethyl, 2-hydroxypropyl group or mixtures thereof;

R$_2$ is a C$_6$–C$_{24}$ straight or branched chain, saturated or unsaturated hydrocarbon group or mixtures thereof;

X is hydrogen (H), an alkali metal, alkaline earth metal, ammonium group, alkyl ammonium group, mono-, di-, or trialkanol ammonium group, basic amino acid or mixtures thereof;

Y=amine (NH), ether (O), ester (COO or OOC), amide (NR$_1$CO, CONR$_1$ or NCOR$_1$), hydroxy (CHOH or C(OH)$_2$) group or mixtures thereof;

n=1–6;

m=1–6;

p=0–25; and

Z=hydrogen (H) or hydrogen and at least one methyl group.

10. A sulfated heteroatom containing aldonamide according to claim 9, wherein:

G is a mixture of hydrogen (H) and at least one SO$_3$X group;

R$_1$ is hydrogen (H), a C$_1$–C$_6$ hydrocarbon, 2-hydroxyethyl, 2-hydroxypropyl group or mixtures thereof;

R$_2$ is a C$_8$–C$_{22}$ straight or branched chain, saturated or unsaturated hydrocarbon group or mixtures thereof;

X is hydrogen (H), an alkali metal, alkaline earth metal, ammonium group, alkyl ammonium group, mono-, di-, or trialkanol ammonium group, basic amino acid or mixtures thereof;

Y=ether (O), amide (NR$_1$CO, CONR$_1$ or NCOR$_1$), hydroxy (CHOH or C(OH)$_2$) group or mixtures thereof;

n=1–5;

m=1–5;

p=0–5; and

Z=hydrogen (H) or hydrogen and at least one methyl group.

11. A sulfated heteroatom containing aldonamide according to claim 8 having the formula:

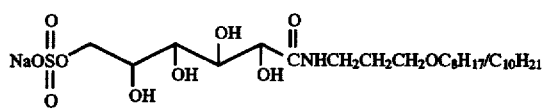

wherein:

G is a mixture of hydrogen (H) and one SO$_3$X group;

R$_1$ is hydrogen (H);

R$_2$ is C$_6$H$_{13}$ (1%), C$_8$H$_{17}$ (59%), C$_{10}$H$_{21}$ (39%), C$_{12}$H$_{25}$ (1%);

X is sodium (Na);

Y is oxygen (O);

n=4;

m=3;

p=0;

and Z=hydrogen (H).

12. A sulfated heteroatom containing aldonamide according to claim 8 having the formula:

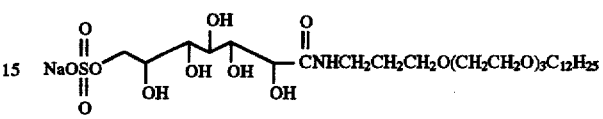

wherein:

G is a mixture of hydrogen (H) and one SO$_3$X group;

R$_1$ is hydrogen (H);

R$_2$ is C$_{12}$H$_{25}$;

X is sodium (Na);

n=5;

m=3;

p=0;

and Z=hydrogen (H).

13. A sulfated heteroatom containing aldonamide according to claim 8 having the formula:

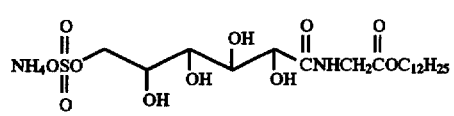

wherein:

G is a mixture of hydrogen (H) and one SO$_3$X group;

R$_1$ is hydrogen (H);

R$_2$ is CH$_2$OC$_{13}$H$_{25}$;

X is ammonium (NH$_4$);

n=4;

m=1;

p=0;

and Z=hydrogen (H).

14. A disulfated heteroatom containing aldonamide according to claim 8 having the formula:

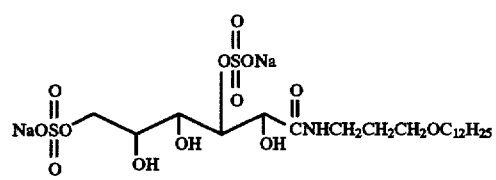

wherein:

G is a mixture of hydrogen (H) and two SO$_3$X groups;

R$_1$ is hydrogen (H);

R$_2$ is (CH$_2$)$_3$OC$_{12}$H$_{25}$;

X is sodium (Na);

n=4;

m=3;

p=0;

and Z=hydrogen (H).

15. A sulfated alkyl(glycosid)uronamide having the formula:

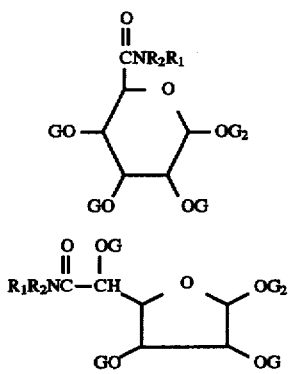

wherein:
G is a mixture of hydrogen (H) and at least one $SO_3X$ group, or a mixture of hydrogen (H), polyoxyethylene, polyoxypropylene and at least one $SO_3X$ group;

$G_2$ is a mixture of hydrogen (H) and at least one $SO_3X$ group, a mixture of hydrogen (H), polyoxyethylene, polyoxypropylene and at least one $SO_3X$ group or a mixture of a $C_1$–$C_{18}$ hydrocarbon and at least one $SO_3X$ group;

$R_1$ is hydrogen (H), a $C_1$–$C_{18}$ straight or branched chain, saturated or unsaturated hydrocarbon group or mixtures thereof;

$R_2$ is a $C_1$–$C_{26}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$, wherein $R_1$ is defined as $R_1$ above), sulfamate ($NSO_3X$), hydroxy (CHOH or $C(OH)_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

16. A sulfated alkyl(glycosid)uronamide according to claim 15, wherein:

$G_2$ is a mixture of hydrogen (H) and at least one $SO_3X$ group, a mixture of hydrogen (H), or a mixture of a $C_1$–$C_8$ hydrocarbon and at least one $SO_3X$ group;

$R_1$ is hydrogen (H), a $C_1$–$C_8$ hydrocarbon, 2-hydroxyethyl, 2-hydroxypropyl group or mixtures thereof;

$R_2$ is a $C_6$–$C_{24}$ straight or branched chain, saturated or unsaturated hydrocarbon group that may be interrupted with at least one heteroatom selected from the group consisting of amine (NH), ether (O), ester (COO or OOC), amide ($NR_1CO$, $CONR_1$ or $NCOR_1$), hydroxy (CHOH or $C(OH)_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

17. A sulfated alkyl(glycosid)uronamide according to claim 15, wherein

G is a mixture of hydrogen (H) and at least one $SO_3X$ group;

$G_2$ is a mixture of hydrogen (H) and at least one $SO_3X$ group, a mixture of hydrogen (H), or a mixture of a $C_1$–$C_6$ hydrocarbon and at least one $SO_3X$ group;

$R_1$ is hydrogen (H), a $C_1$–$C_6$ hydrocarbon, 2-hydroxyethyl, 2-hydroxypropyl group or mixtures thereof;

$R_2$ is a $C_8$–$C_{22}$ straight or branched chain, saturated or unsaturated hydrocarbon group that may be interrupted with at least one heteroatom selected from the group consisting of ether (O), amide ($NR_1CO$, $CONR_1$ or $NCOR_1$), hydroxy (CHOH or $C[OH]_2$) or mixtures thereof; and X is hydrogen (H), an alkali metal, alkaline earth metal, ammonium group, alkyl ammonium group, mono-, di-, or trialkanol ammonium group, basic amino acid or mixtures thereof.

18. A sulfated alkyl(glycosid)uronamide according to claim 15 having the formula:

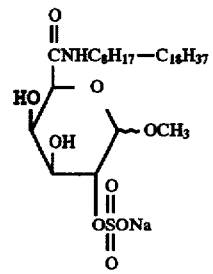

wherein:

G is a mixture of hydrogen (H) and one $SO_3X$ group;

$G_2$ is methyl ($CH_3$);

$R_1$ is hydrogen (H);

$R_2$ is $C_8H_{17}$ (5%), $C_{10}H_{21}$ (7%), $C_{12}H_{25}$ (50%), $C_{14}H_{29}$ (18%), $C_{16}H_{33}$ (10%), $C_{18}H_{37}$ (6%), $C_{18}H_{35}$ (4%);

and X is sodium (Na).

19. A sulfated alkyl (glycosid)uronamide according to claim 15 having the formula:

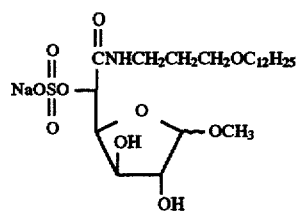

wherein:

G is a mixture of hydrogen (H) and one $SO_3X$ group;

$R_1$ is hydrogen (H);

$R_2$ is $(CH_2)_3OC_{12}H_{25}$;

$G_2$ is methyl ($CH_3$);

and X is sodium (Na).

20. A sulfated alkyl(glycosid)uronamide according to claim 15 having the formula:

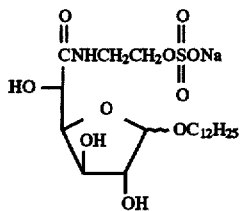

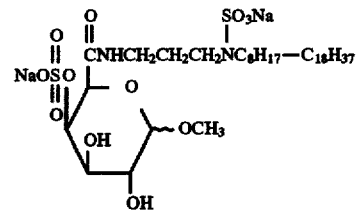

wherein:

G is a mixture of hydrogen (H) and one SO$_3$X group;

R$_1$ is hydrogen (H);

R$_2$ is (CH$_2$)$_3$OC$_{12}$H$_{25}$;

G$_2$ is methyl (CH$_3$);

and X is sodium (Na).

21. A sulfated alkyl(glycosid)uronamide according to claim 15 having the formula:

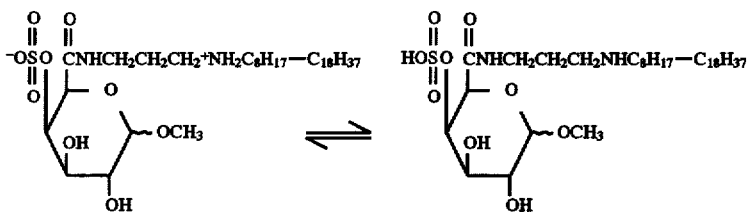

wherein:

G is a mixture of hydrogen (H) and one SO$_3$X group;

G$_2$ is methyl (CH$_3$);

R$_1$ is hydrogen (H);

R$_2$ is (CH$_2$)$_3$NHC$_8$H$_{17}$ (5%), (CH$_2$)$_3$NHC$_{10}$H$_{21}$ (7%), (CH$_2$)$_3$NHC$_{12}$H$_{25}$ (50%), (CH$_2$)$_3$NHC$_{14}$H$_{29}$ (18%), (CH$_2$)$_3$NHC$_{16}$H$_{33}$ (10%), (CH$_2$)$_3$NHC$_{18}$H$_{37}$ (6%), (CH$_2$)$_3$NHC$_{18}$H$_{35}$ (4%);

and X is hydrogen (H).

22. A sulfated alkyl(glycosid)uronamide according to claim 15 having the formula:

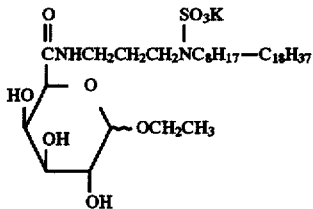

wherein:

G is hydrogen (H);

G$_2$ is ethyl (CH$_2$CH$_3$);

R$_1$ is hydrogen (H);

R$_2$ is (CH$_2$)$_3$N(SO$_3$K)C$_8$H$_{17}$ (5%), (CH$_2$)$_3$N(SO$_3$K)C$_{10}$H$_{21}$ (7%), (CH$_2$)$_3$N(SO$_3$K)C$_{12}$H$_{25}$ (50%), (CH$_2$)$_3$N(SO$_3$K)C$_{14}$H$_{29}$ (18%), (CH$_2$)$_3$N(SO$_3$K)C$_{16}$H$_{33}$ (10%), (CH$_2$)$_3$N(SO$_3$K)C$_{18}$H$_{37}$ (6%), (CH$_2$)$_3$N(SO$_3$K)C$_{18}$H$_{35}$ (4%);

and X is potassium (K).

23. A disulfated alkyl(glycosid)uronamide according to claim 15 having the formula:

wherein:

G is a mixture of hydrogen (H) and two SO$_3$X groups;

G$_2$ is methyl (CH$_3$);

R$_1$ is hydrogen (H);

R$_2$ is (CH$_2$)$_3$N(SO$_3$Na)C$_8$H$_{17}$ (5%), (CH$_2$)$_3$N(SO$_3$Na)C$_{10}$H$_{21}$ (7%), (CH$_2$)$_3$N(SO$_3$Na)C$_{12}$H$_{25}$ (50%), (CH$_2$)$_3$N(SO$_3$Na)C$_{14}$H$_{29}$ (18%), (CH$_2$)$_3$N(SO$_3$Na)C$_{16}$H$_{33}$ (10%), (CH$_2$)$_3$N(SO$_3$Na)C$_{18}$H$_{37}$ (6%), (CH$_2$)$_3$N(SO$_3$Na)C$_{18}$H$_{35}$ (4%);

and X is sodium (Na).

24. A process for producing sulfated alkyl aldobionamides, sulfated heteroatom containing alkyl aldonamides, or sulfated alkyl(glycosid)uronamides comprising the steps of:

(1) preparing a heterogeneous suspension or homogeneous solution comprising of a mixture of alkyl aldobionamide, heteroatom containing alkyl aldonamide or alkyl (glycosid)uronamide and organic solvent;

(2) adding a sulfating agent to said polyhydroxyamide suspension or solution such that the molar ratio of sulfating agent to polyhydroxyamide is from about 10:1 to about 1:10;

(3) allowing the sulfating agent and polyhydroxyamide suspension or solution to react under rapid agitation until deemed complete;

(4) removing the solvent by distillation or allowing the water to remain with the finished product for use as a diluent.

25. A process according to claim 24 wherein, after adding the sulfating agent (step (2)), the mixture of sulfating agent and the polyhydroxyamide suspension or solution is reacted at a temperature of −30° C. to about 100° C.

26. A process according to claim 24 wherein, after the sulfating agent and polyhydroxyamide suspension or solution are reacted to completion (step (3)), the organic solvent is removed by distillation or inert gaseous sparge.

27. A process according to claim 24 wherein, after step (3), water or aqueous solvent system are added and the resulting sulfated alkyl aldobionamide, sulfated heteroatom containing alkyl aldonamide or sulfated alkyl(glycosid) uronamide is neutralized with base.

28. A process according to claim 27 wherein, after neutralization with base, there is followed treatment with a bleaching or reducing agent at temperature about from 0° C. to 50° C.

29. A process according to claim 24, wherein the solvent is selected from the group consisting of:

chloroform, 1-chlorobutane, 1,2-dichloroethane, dichloromethane, trichloroethylene, tetrachloroethylene, carbon tetrachloride, 1,2,2-trichloro-1,2,2-trifluoroethane, 1-chloro-1,1-difluoroethane; toluene, xylene, dichlorobenzene, ethylbenzene, isopropylbenzene; dimethylformamide, dimethylacetamide, pyridine, diethylamine, triethylamine, trimethylamine ethyl ether, butyl ether, t-butyl methyl ether, petroleum ether, ethylene glycol dimethyl ether, tetrahydrofuran and thioxane and mixtures thereof.

30. A process according to claim 24, wherein the molar ratio of sulfating agent to said polyhydroxyamide is from about 8:1 to about 1:5.

31. A process according to claim 24, wherein the molar ratio of sulfating agent to said polyhydroxyamide is from about 5:1 to about 1:3.

32. A process according to claim 25, wherein the temperature of the reaction is from −20° C. to about 70° C.

33. A process according to claim 25, wherein the temperature of the reaction is from about −10° C. to about 50° C.

34. A process according to claim 27, wherein the base is selected from the group consisting of:
sodium hydroxide, potassium hydroxide, sodium carbonate, sodium bicarbonate, ammonium hydroxide, magnesium hydroxide, lithium hydroxide, calcium hydroxide, sodium methoxide, sodium ethoxide, ammonia, monoethanolamine, diethanolamine, triethanolamine, methylamine, dimethylamine, triethylamine, methyl glucamine, glucamine, chitosamine (glucosamine), 2-amino-2-ethyl-1-3-propanediol, tris(hydroxymethyl) aminomethane, sodium glycinate, potassium glycinate, ammonium glycinate, sodium alaninate, sodium lysinate, potassium lysinate, sodium methioninate, sodium prolinate, sodium serinate, sodium asparaginate; sodium glutaminate, 1-amino-2-propanol, 2-amino-2-methylpropanol, tris-(hydroxyethyl)amine, 3-amino-1,3-propanediol, 3-methylamino-1,3-propanediol and mixtures thereof.

35. A process according to claim 28, wherein the bleaching agent is selected from the group consisting of:
hydrogen peroxide, sodium hypochlorite, potassium hypochlorite, calcium hypochlorite, lithium hypochlorite, dibasic magnesium hypochlorite, sodium hypobromite, chlorinated trisodium phosphate, hypochlorous acid, chlorine dioxide, sodium perborate, sodium percarbonate, potassium percarbonate, oxone, t-butyl hydroperoxide, benzoylperoxide, bis(trimethylsilyl)peroxide, peroxymonosulfate, peroxyformic acid, peroxyacetic acid, peroxytrifluoroacetic acid, peroxybenzoic acid, m-chloroperoxybenzoic acid, peroxyphthalic acid, peroxypropionic acid, peroxylauric acid and mixtures thereof.

36. A process according to claim 28, wherein the reducing agent is selected from the group sodium sulfite, potassium sulfite, calcium sulfite, sodium bisulfite(sodium hydrogen sulfite), potassium bisulfite, sodium hydrosulfite, zinc hydrosulfite, sodium metabisulfite, potassium metabisulfite sodium hydride, potassium hydride, lithium hydride, magnesium hydride, calcium hydride, sodium borohydride, sodium cyano borohydride, lithium borohydride, potassium borohydride, magnesium borohydride, alkyl- and alkoxy borohydrides, diborane, sodium aluminum hydride, potassium aluminum hydride, calcium aluminum hydride, lithium aluminum hydride and mixtures thereof.

37. A process according to claim 28, wherein the bleaching or reducing agent is added at a level from about 0.01% to about 7% by weight of the reaction mixture.

38. A process according to claim 24, wherein the sulfating agent is selected from the group consisting of bromosulfonic acid, chlorosulfonic acid, urea chlorosulfonic acid complex, sulfuric acid, urea sulfur acid complex, oleum, sulfamic acid, sulfur trioxide, dioxane sulfur trioxide complex and sulfur trioxide Lewis base complexes such as sulfur trioxide triethylamine complex, sulfur trioxide pyridine complex, sulfur trioxide urea complex and mixtures thereof.

39. A process according to claim 34, wherein the sulfating agent is selected from the group consisting of:
chlorosulfonic acid, sulfur trioxide, sulfur trioxide pyridine complex and mixtures thereof.

40. A process for improving the color of alkyl aldonamides comprising of the steps of:
(1) preparing a heterogeneous suspension or homogeneous solution comprising of a mixture of alkyl aldonamide and organic solvent;
(2) adding a sulfating agent to alkyl aldonamide suspension or solution such that the molar ratio of sulfating agent to alkyl aldonamide is from about 10:1 to about 1:10;
(3) allowing the sulfating agent and alkyl aldonamide suspension or solution to react under rapid agitation until deemed complete to form sulfated alkyl aldonamide;
(4) treating the sulfated alkyl aldonamide with a bleaching or reducing agent at a temperature from about 0° C. to about 50° C.; and
(5) removing the organic solvent by distillation on allowing the water to remain with the finished product for use as a diluent.

41. A process according to claim 40 wherein after step (2), the mixtures of sulfating agent and alkyl aldonamide suspension or solution is reacted at temperatures from about −30° C. to 100° C.

42. A process according to claim 41 wherein after step (3), the organic solvent is removed by distillation or inert gaseous sparge.

43. A process according to claim 40 wherein, after step (3), water or aqueous solvent systems are added and the resulting sulfated alkyl aldonamide is neutralized with base.

* * * * *